US012582782B2

(12) United States Patent
Arnell et al.

(10) Patent No.: US 12,582,782 B2
(45) Date of Patent: Mar. 24, 2026

(54) DRY SALT THERAPY DEVICE WITH CONVERGING-DIVERGING NOZZLE

(71) Applicant: My Friend the Sea, LLC, Katonah, NY (US)

(72) Inventors: Sara Arnell, Katonah, NY (US); Jason M. Lundy, New York, NY (US); Carlos R. Lamarche, New York, NY (US); Pepin Sebastian Gelardi, Richmond, VA (US); Theodore Regan Ullrich, New York, NY (US); Julia Grace Timko, Brooklyn, NY (US); Man Fung Tse, New York, NY (US)

(73) Assignee: My Friend the Sea, LLC, Katonah, NY (US)

( * ) Notice: Subject to any disclaimer, the term of this patent is extended or adjusted under 35 U.S.C. 154(b) by 837 days.

(21) Appl. No.: 17/886,784

(22) Filed: Aug. 12, 2022

(65) Prior Publication Data

US 2023/0293829 A1 Sep. 21, 2023

Related U.S. Application Data

(60) Provisional application No. 63/304,084, filed on Jan. 28, 2022.

(51) Int. Cl.
*A61M 15/00* (2006.01)
*A61K 33/14* (2006.01)
(Continued)

(52) U.S. Cl.
CPC ........... *A61M 15/002* (2014.02); *A61K 33/14* (2013.01); *A61M 15/0086* (2013.01); *B05B 7/00* (2013.01);
(Continued)

(58) Field of Classification Search
CPC .... A61M 15/00; A61M 15/02; A61M 15/002; A61M 15/0086; A61M 2205/07;
(Continued)

(56) References Cited

U.S. PATENT DOCUMENTS 5,337,740 A * 8/1994 Armstrong ........ A61M 15/0041
128/203.15
6,651,654 B2 11/2003 Rogacki
(Continued)

FOREIGN PATENT DOCUMENTS

KR 2015-0003148 U 8/2015
RU 2 027 447 C1 1/1995
(Continued)

OTHER PUBLICATIONS

[No Author Listed] "HaloSmart-01" Halogenerator. Halomed. http://www.halomed.lt/en/products/36-halosmart-01-halogenerator. Publicly available at least as early as Aug. 12, 2022.
(Continued)

*Primary Examiner* — Brandy S Lee
*Assistant Examiner* — Rohan Patel
(74) *Attorney, Agent, or Firm* — Wolf, Greenfield & Sacks, P.C.

(57) ABSTRACT

A dry salt therapy device includes a blower, an exhaust passage fluidly coupled to the blower, a grinding chamber configured to aerosolize salt, and a salt vent fluidly coupling the exhaust passage and the grinding chamber. A flow structure may be provided. The grinding chamber may have a particular aspect ratio, tip clearance, or floor clearance. Salt may be delivered to a user without contacting the user, the salt being delivered in a jet having a particular diameter at a particular distance. The device can include a converg- (Continued)

ing-diverging nozzle in the exhaust passage. The salt vent may protrude into a center of a flow of air through the exhaust passage.

19 Claims, 17 Drawing Sheets

(51) Int. Cl.

| | |
|---|---|
| *B05B 7/00* | (2006.01) |
| *A61M 11/00* | (2006.01) |
| *A61M 11/02* | (2006.01) |
| *A61M 16/00* | (2006.01) |

(52) U.S. Cl.
CPC ............ *A61M 11/002* (2014.02); *A61M 11/02* (2013.01); *A61M 16/0066* (2013.01); *A61M 2202/066* (2013.01); *B05B 7/0075* (2013.01)

(58) Field of Classification Search
CPC ...... A61M 16/0066; A61M 2205/3365; A61M 11/001; A61M 11/002; A61M 11/02; A61M 2206/14; A61M 2206/10; A61M 2206/20; A61K 33/14; B05B 7/1459; B05B 7/0075
See application file for complete search history.

(56) References Cited

U.S. PATENT DOCUMENTS

| | | | |
|---|---|---|---|
| 7,802,569 | B2 | 9/2010 | Yeates et al. |
| 8,282,019 | B2 | 10/2012 | Karimi Esfahani et al. |
| 8,955,777 | B2 | 2/2015 | Viherlahti |
| 9,629,968 | B2 | 4/2017 | Monterenzi |
| 9,764,103 | B2 | 9/2017 | Neff et al. |
| 10,449,836 | B2 | 10/2019 | Lee et al. |
| 10,583,261 | B2 | 3/2020 | Ohrt et al. |
| 10,987,999 | B2 | 4/2021 | Wokrinek et al. |
| 11,779,943 | B1 * | 10/2023 | Thomas, Jr. .......... B05B 1/3402 239/11 |

| | | | |
|---|---|---|---|
| 2008/0163871 | A1 | 7/2008 | Bozoky et al. |
| 2017/0072150 | A1 | 3/2017 | Lankau et al. |
| 2021/0077756 | A1 * | 3/2021 | Hilliard ............. A61M 16/0066 |
| 2021/0205549 | A1 | 7/2021 | Kokai |

FOREIGN PATENT DOCUMENTS

| | | | | |
|---|---|---|---|---|
| WO | WO-0234320 A1 * | 5/2002 | ........ | A61M 15/0065 |
| WO | WO-2008084269 A2 * | 7/2008 | ........ | A61M 15/0083 |

OTHER PUBLICATIONS

[No Author Listed] HaloPocket Halotherapy in your pocket: Introducing the smallest salt therapy option in the world. Halotherapy Solutions. https://halotherapysolutions.com/portable-halotherapy/. Publicly available at least as early as Aug. 12, 2022. 3 pages.

[No Author Listed] IIRIS-137 Halogenerator for home use. Kokkonen LLC. https://salt-cocoon.com/products/iiris-137-portable-halogenerator-for-home-use/. Publicly available at least as early as Aug. 12, 2022. 1 page.

[No Author Listed] Introducing the most convenient and affordable way to breathe easier. Salt Therapy Home, LLC. https://salttherapyhome.com/?utm_source=organic&utm_medium=website&utm_campaign=Salt%20Therapy%20Home&utm_content=sth-website. Publicly available at least as early as Aug. 12, 2022. 5 pages.

[No Author Listed] ISR Pro Salt Air Machine. Infinity Salt Air. https://infinitysaltair.com/products/isr-pro. Publicly available at least as early as Aug. 12, 2022. 2 pages.

[No Author Listed] Prizma Prizsalt+S. Prizma. https://www.prizma.rs/en/products/halogenerators/wellness-spa-device/prizma-prizsalt-s-plus.html. Publicly available at least as early as Aug. 12, 2022. 2 pages.

[No Author Listed] The Halo. GuruNanda, LLC. https://gurunanda.com/collections/diffusers/products/guru-nanda-halo-xl-humidifier-essential-oil-diffuser?gclid=EAIaIQobChMIw5Pf35D88gIVogaICR0BxQkfEAQYAiABEgLX8_D_BwE. Publicly available at least as early as Mar. 5, 2022. 2 pages.

* cited by examiner

DRY SALT THERAPY DEVICE WITH CONVERGING-DIVERGING NOZZLE

RELATED APPLICATION

This application claims the benefit under 35 U.S.C. § 119(e) to U.S. Provisional Application Ser. No. 63/304,084, entitled "DRY SALT THERAPY DEVICE," filed on Jan. 28, 2022, which is herein incorporated in its entirety.

FIELD

Disclosed embodiments are related to dry salt therapy devices.

BACKGROUND

Dry salt therapy, also known as halotherapy, is a respiratory therapy that delivers salt particles into a user's respiratory system. For nearly 200 years, dry salt therapy has been used to treat a variety of respiratory ailments including asthma, bronchitis, pneumonia, cystic fibrosis, sinusitis, and hay fever. Dry salt therapy also provides benefits related to anxiety, fatigue, and stress, as well as skin conditions such as acne, eczema, psoriasis, dermatitis, rosacea, dryness, rashes, and inflammation. Dry salt therapy can be provided using dry salt therapy devices, or halogenerators. Dry salt therapy devices may deliver salt particles to a user's respiratory system through the air.

SUMMARY

In some embodiments, a dry salt therapy device may comprise a blower, an exhaust passage fluidly coupled to the blower, a grinding chamber configured to aerosolize salt, the grinding chamber having an aspect ratio between 4:1 and 8:1, a tip clearance between 1 mm and 5 mm, and a floor clearance between 1 mm and 4 mm. The device may further comprise a salt vent configured to fluidly couple the exhaust passage and the grinding chamber.

In other embodiments, a dry salt therapy device may comprise a blower, an exhaust passage fluidly coupled to the blower, a grinding chamber configured to aerosolize salt, and a salt vent configured to fluidly couple the exhaust passage and the grinding chamber. The device may be configured to deliver a jet of aerosolized salt to a respiratory system of a user without being in contact with the user. The jet may have a diameter of between 4 inches and 8 inches at a distance of between 2 feet and 4 feet.

In further embodiments, a dry salt therapy device may comprise a blower, an exhaust passage fluidly coupled to the blower, the exhaust passage comprising a converging-diverging nozzle including a converging section, a throat section, and a diverging section. The device may further comprise a grinding chamber configured to aerosolize salt, and a salt vent configured to fluidly couple the exhaust passage and the grinding chamber.

In still further embodiments, a dry salt therapy device may comprise a blower, an exhaust passage fluidly coupled to the blower, a flow structure disposed in the exhaust passage and configured to modify a flow of air through the exhaust passage, a grinding chamber configured to aerosolize salt, and a salt vent configured to fluidly couple the exhaust passage and the grinding chamber.

In some embodiments, a dry salt therapy device may comprise a blower, an exhaust passage fluidly coupled to the blower, a grinding chamber configured to aerosolize salt, and a salt vent configured to fluidly couple the exhaust passage and the grinding chamber, the salt vent protruding from a wall of the exhaust passage into a center of a flow of air through the exhaust passage.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
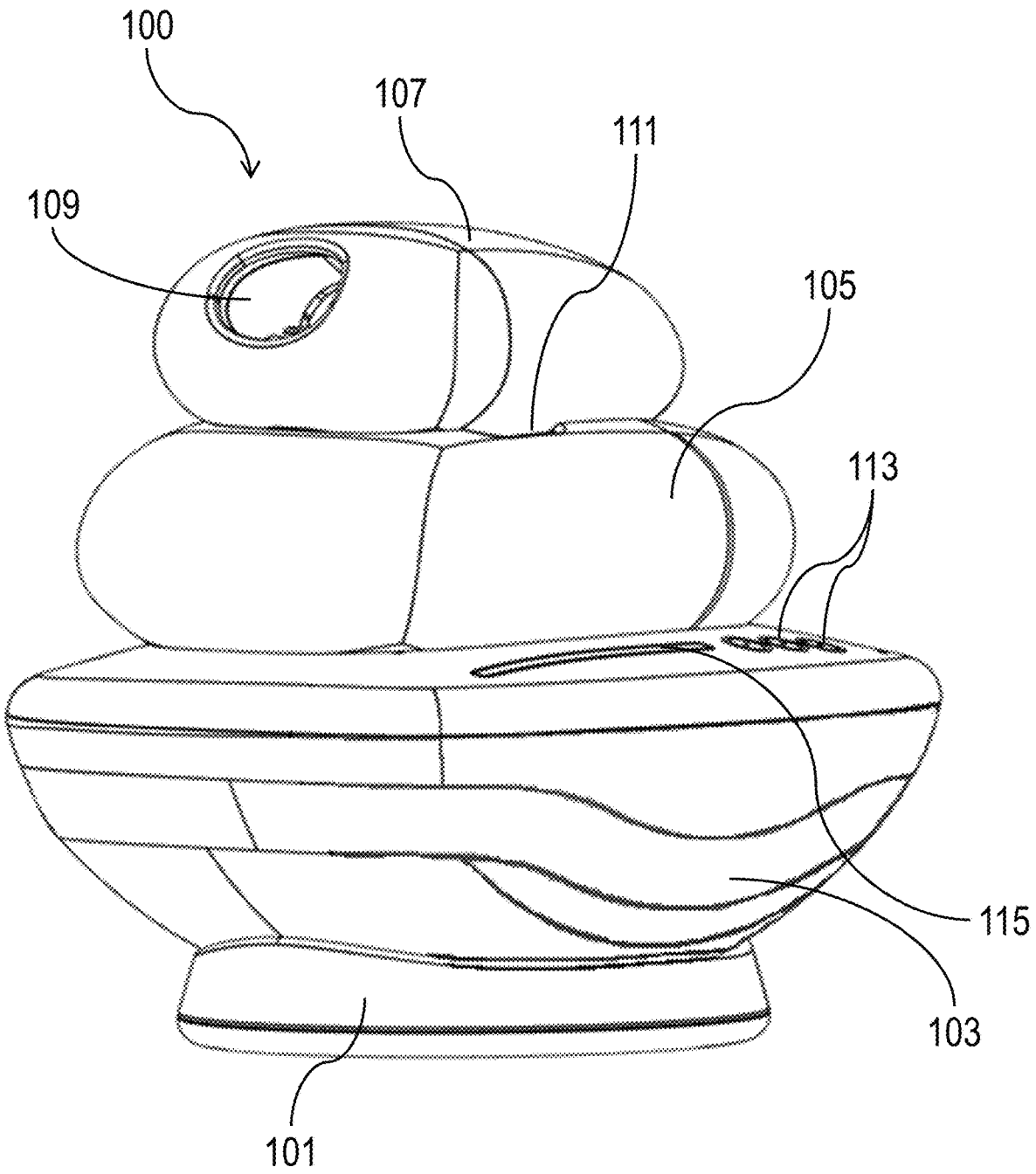
FIG. 1 is a front perspective view of one embodiment of a dry salt therapy device.

Dry salt therapy devices (or halogenerators) allow users to obtain the benefits of dry salt therapy at home or another location without requiring the user to travel to a dedicated dry salt therapy facility. When used for respiratory benefits, dry salt therapy devices operate by delivering salt particles to a user's respiratory system through the air. The salt particles may be delivered indirectly by diffusing salt particles into an enclosed area, sometimes referred to as a dry salt therapy room, a dry salt therapy tent, or a dry salt therapy cave. The salt particles may also be delivered directly to the respiratory system using a mask or a nozzle, or by holding the device close to the user's face.

The size of the salt particles may affect the efficacy of the dry salt therapy treatment. For example, salt particles of 1-5 microns have been studied in the treatment of asthma and chronic obstructive pulmonary disease (COPD). A dry salt therapy device may provide salt particles of a desired size in two ways. In the first method, the salt particles may be the appropriate size before they are loaded into the device. In this case, the device may simply generate a flow of air on which to carry the pre-sized salt particles. In the second method, the dry salt therapy device may accept larger salt particles, such as granulated salt, and the device may micronize the larger particles before mixing the micronized salt into a flow of air, thereby aerosolizing the salt particles.

The benefit of this second method is that a user need not obtain salt particles that have been specially prepared or pre-micronized. Instead, a user may load a dry salt therapy device with common forms of salt such as table salt. This may reduce the costs and complexity of dry salt therapy treatment. However, the drawbacks of using the dry salt therapy device to micronize the salt include design complexities associated with building a device capable of accepting common forms of salt, micronizing the salt down to an appropriate size, and mixing the micronized salt particles into a flow of air to be delivered to a user. These design complexities may limit the particle size that may be achieved. For example, current systems may achieve a particle size of around 5 microns. However, a particle size of around 1-3 microns or around 0.5-1.5 microns may result in greater benefits to a user.

In view of the above, the inventors have recognized the benefits of using a compact grinding chamber to micronize salt particles. In some embodiments, the grinding chamber may have an aspect ratio between 4:1 and 8:1. As used herein, the aspect ratio of the grinding chamber may be defined as a ratio of a diameter of the chamber to a height of the chamber. In other embodiments, the grinding chamber may contain a grinding rotor. Furthermore, in some embodiments, a tip clearance of between 1 mm and 5 mm may be provided. As used herein, the tip clearance of the grinding chamber may be defined as a space between a tip of a blade of the grinding rotor and an interior wall of the grinding chamber. In other embodiments, a floor clearance of between 1 mm and 4 mm may be provided. As used herein, the floor clearance of the grinding chamber may be defined as a space between a bottom surface of the grinding rotor and a floor of the grinding chamber. In some embodiments, the grinding rotor may be configured to rotate at a speed between 3,000 rotations per minute (RPM) and 4,500 RPM. In some embodiments, a grinding chamber may micronize salt particles to a particle size of between 0.5 microns and 1.5 microns.

Dry salt therapy devices may deliver salt particles, whether pre-micronized or micronized by the device, to a user's respiratory system in two ways. First, the device may disperse salt into the surrounding atmosphere, diffusing salt through the space around the device. This may be done in a dedicated space or enclosure. Such enclosures are sometimes referred to as salt rooms or salt tents. The second method of delivery requires the device to deliver the salt particles directly to the user's respiratory system. Such devices may use masks, which must be attached to the user's face, thereby restricting the user's movement during a dry salt therapy session. Other such devices may discharge a narrow stream of aerosolized salt. However, these devices must be held by the user (or another person) to ensure that the narrow stream is delivered to the correct area (i.e., the user's nose and/or mouth).

In view of the above, the inventors have recognized the benefits of a dry salt therapy device that delivers a jet of aerosolized salt to a user's face from a distance away from the user. Such devices do not require the user to be connected to or in contact with the device, allowing the user to move freely during a dry salt therapy session. In some embodiments, the jet may have a diameter of between 4 inches and 8 inches at a distance of between 2 feet and 4 feet.

In some embodiments, a dry salt therapy device may comprise one or more housing modules, a device air inlet, a blower, an exhaust passage, a device outlet, a salt vent, a grinding chamber, and a grinding chamber air inlet. In operation, a dose of granulated salt may be loaded into the grinding chamber and the device may be powered on. Powering on the device may cause the motor to micronize or aerosolize the granulated salt by turning the grinding rotor, and may cause the blower to activate. Activation of the blower may generate a flow of air through the blower. Air may enter the dry salt therapy device through the device inlet, and may be drawn through the blower into the exhaust passage. The exhaust passage may contain a salt vent that may be fluidly coupled to the grinding chamber, thereby allowing aerosolized salt to be drawn out of the grinding chamber and into the exhaust passage in response to the flow of air passing through the exhaust chamber. The grinding chamber may have an air inlet to allow replacement air to be drawn into the grinding chamber as the aerosolized salt is drawn out through the salt vent. A jet of aerosolized salt may be delivered through the device outlet to a respiratory system of a user.

In some embodiments, the exhaust passage may comprise a converging-diverging (CD) nozzle. In such embodiments, a diameter or width of the exhaust passage may decrease through a converging section until it reaches a minimum in a throat section of the CD nozzle. Downstream of the throat section, the diameter of the exhaust passage may increase through a diverging section. The diverging section may terminate at the device outlet. In such embodiments, the salt vent may be disposed in or near the throat section. In some embodiments, the salt vent may protrude from a wall of the exhaust passage into a center of the flow of air. In other embodiments, the salt vent may be disposed in either a converging section or a diverging section of the CD nozzle.

In some embodiments, the device may include a flow structure within the exhaust passage to modify the flow of air. In some embodiments, the flow structure may be disposed in the converging section. In some embodiments, the flow structure may be disposed immediately upstream of a salt vent. In such embodiments, the flow structure may increase a pressure difference between a point in the exhaust passage and a point in the grinding chamber.

The flow structure may be formed in any geometric configuration and may be disposed at any point along the exhaust passage that produces the desired flow characteristic. For example, a flow structure may be used to increase a velocity in a flow of air at a point near the salt vent or to reduce a turbulence within the flow of air. In some embodiments, a flow structure may comprise a first teardrop body and a second teardrop body, each of the first and second teardrop bodies having a tapered end and a rounded end. The rounded ends may be axially connected by an elongate member. The flow structure may be axially aligned with the flow of air such that the tapered end of the first teardrop body points in an upstream direction and the tapered end of the second teardrop body points in a downstream direction.

The blower, the exhaust passage, the flow structure, and/or the salt vent may be configured relative to one another to produce a desired concentration or flow rate of aerosolized salt. For example, in embodiments in which the salt vent is disposed at or near the throat of a CD nozzle in the exhaust passage, the flow structure may be disposed within the diverging section to modify the flow of air prior immediately upstream of the salt vent. In this example, a flow structure may be used to accelerate the flow of air, thereby decreasing the pressure in the exhaust passage. This may result in a greater pressure difference between the exhaust passage and the grinding chamber, thereby producing a higher flow rate through the salt vent. Conversely, a flow structure may be used to decelerate the flow of air, thereby reducing the pressure difference and producing a lower flow rate through the salt vent.

The blower, the exhaust passage, the flow structure, and/or the device outlet may be configured relative to one another to control a size or strength of the jet of aerosolized salt. For example, some embodiments may use a stronger blower to deliver a jet to a greater distance. Other embodiments may include a converging nozzle in the exhaust passage and a narrow device outlet to deliver a jet that is stronger or narrower.

In some embodiments, a method of using a dry salt therapy device may include loading a dose of salt into a grinding chamber of the device, activating a motor to aerosolize the salt, activating a blower to generate at least one flow of air through the device, and positioning a user at a distance away from the device such that the device delivers a jet of aerosolized salt directly to a respiratory system of the user without the user contacting the device.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

In some embodiments as shown in FIGS. 1-4, a dry salt therapy device 100 may comprise a base 101, a first module 103, a second module 105, and a third module 107. The modular constructions may allow for one region of the device 100 to move relative to another region of the device. In this respect, in one embodiment, one module may move and/or rotate relative to another module. While the present embodiment is depicted as having three modules, any number of modules may be used to house the components of the device. Modules may be formed as a single piece, or as two pieces, or as any number of pieces that may be appropriate. Modules may be formed as separate components and fixedly attached to one another. For example, modules may be attached by snap fit, press fit or threaded fasteners such as screws or bolts. Modules may also be removably attached to one another. For example, the third module 107 may be removably attached to the second module 105 using magnets or snap fits. Modules may also be movably or rotatably attached to one another. In the exemplary embodiment shown, the first module 103 may be configured to rock or tilt within the base 101, such that the device may rotate in the directions indicated by arrow R in FIG. 2. In other embodiments, other modules may be configured to rock or tilt in addition to or instead of the first module 103.

Figure 2:
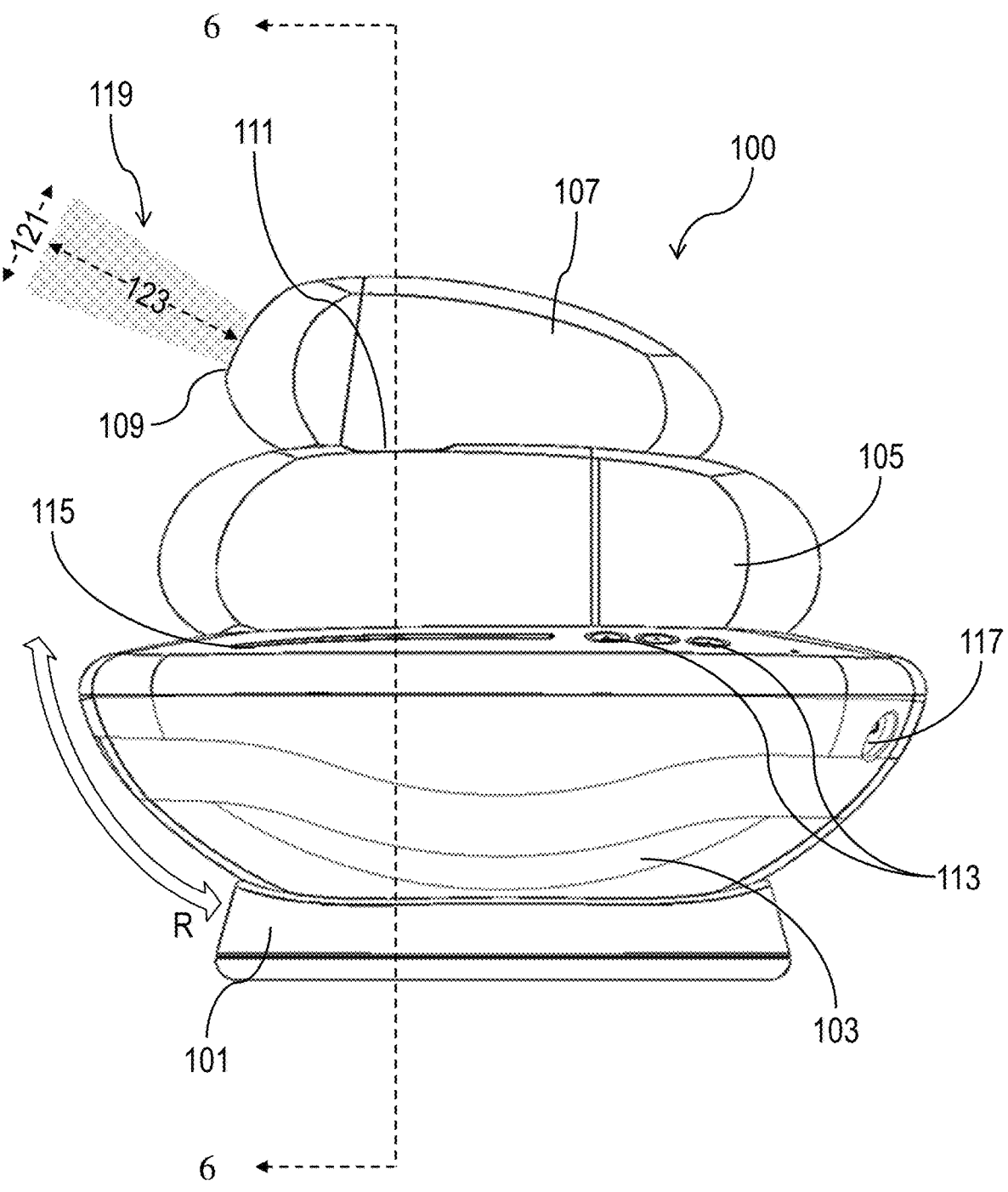
FIG. 2 is a side view of the dry salt therapy device of FIG. 1.
Figure 3:
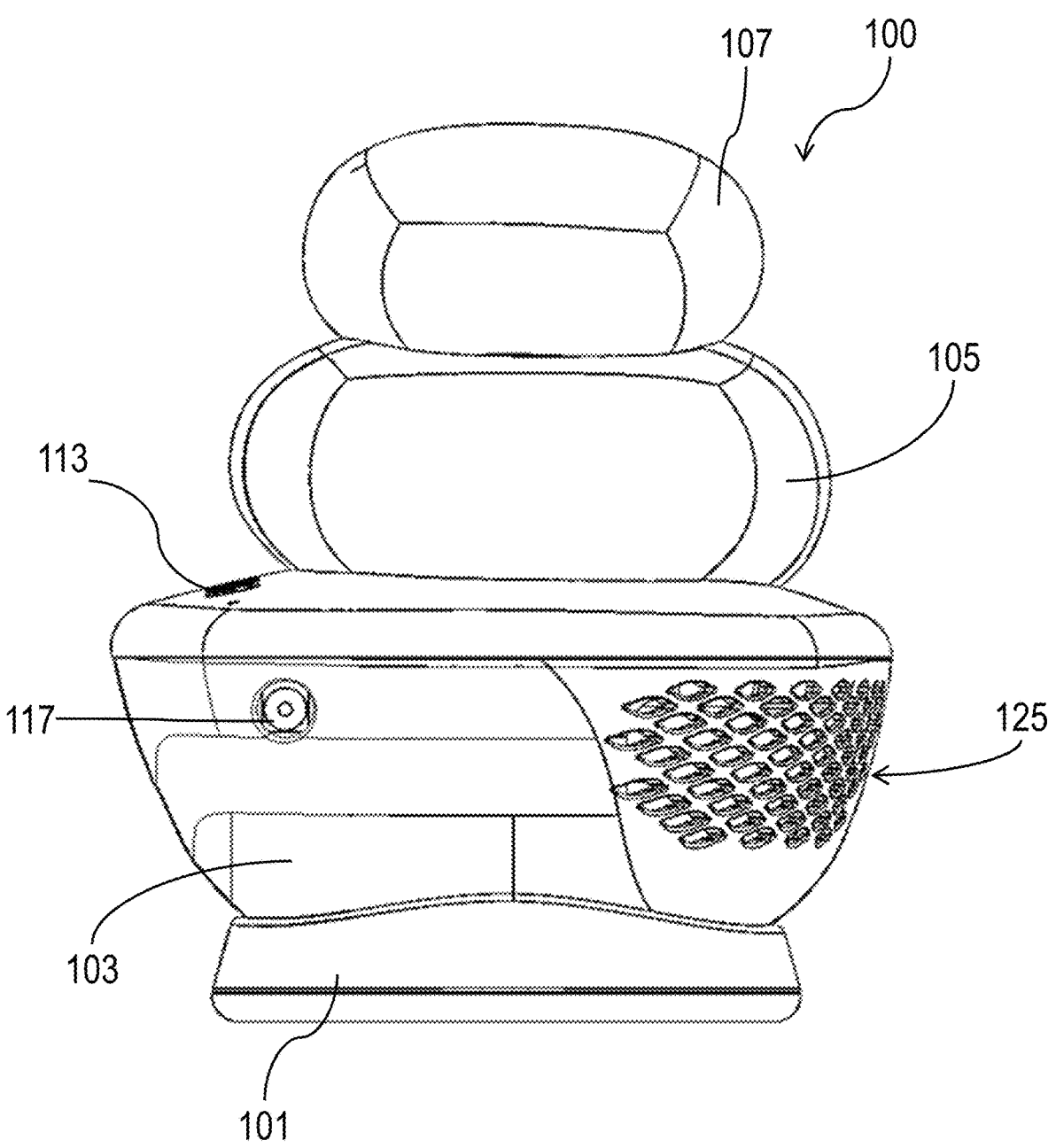
FIG. 3 is a rear view of the dry salt therapy device of FIG. 1.
Figure 4:
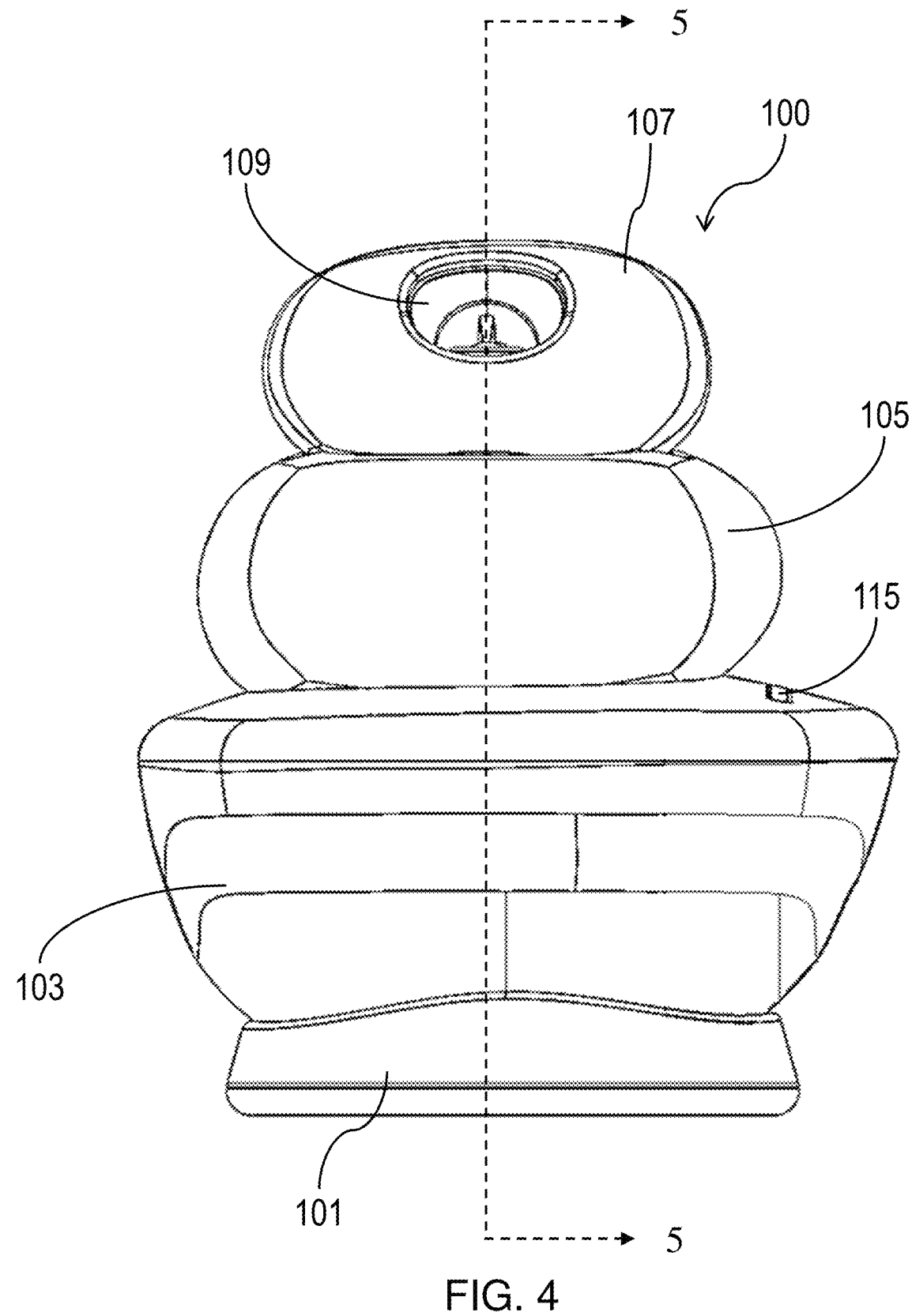
FIG. 4 is a front view of the dry salt therapy device of FIG. 1.

The device 100 may include a device outlet 109 configured to eject a jet 119 of aerosolized salt or air if the salt has been depleted (FIG. 2). In embodiments which include modules as shown, the device outlet 109 may be formed in the third module 107. However, the device outlet may be formed in any appropriate location on the device, as the disclosure is not so limited. The jet 119 may have a jet diameter 121 which may vary along a distance 123 from the device outlet 109. The device 100 may be configured to produce a jet 119 having a desired diameter 121 at a desired distance 123. For example, in some embodiments, a dry salt therapy device may be configured to produce a jet having a desired diameter at a distance greater than or equal to 6 inches, 1 foot, 2 feet, and/or any other appropriate distance from the device. Additionally, the distance may be less than or equal to 3 feet, 4 feet, 6 feet, and/or any other appropriate distance from the device. Combinations of the foregoing are contemplated including, for example, greater than or equal to 6 inches and less than or equal to 6 feet, greater than or equal to 2 feet and less than or equal to 4 feet, and/or any other appropriate combination of the foregoing. Of course, while particular ranges for the jet distance are provided above, it should be understood that other ranges both greater than and less than those noted above are also contemplated as the disclosure is not limited in this fashion.

Additionally, a dry salt therapy device may be configured to produce a jet having a desired diameter greater than or equal to 2 inches, 3 inches, 4 inches, 7 inches, and/or any other appropriate diameter at the desired distance away from the device. Additionally, the diameter may be less than or equal to 8 inches, 10 inches, 14 inches, and/or any other appropriate diameter. Combinations of the foregoing are contemplated including, for example, greater than or equal to 2 inches and less than or equal to 14 inches, greater than or equal to 4 inches and less than or equal to 8 inches, and/or any other appropriate combination of the foregoing. Of course, while particular ranges for the jet diameter are provided above, it should be understood that other ranges both greater than and less than those noted above are also contemplated as the disclosure is not limited in this fashion.

It should also be understood that any range for the jet diameter may be combined with any range for the jet distance. For example, a dry salt therapy device may be configured to produce a jet having: a diameter of greater than or equal to 3 inches and less than or equal to 14 inches at a distance of greater than or equal to 6 inches and less than or equal to 6 feet; a diameter of greater than or equal to 4 inches and less than or equal to 8 inches at a distance of greater than or equal to 2 feet and less than or equal to 4 feet; and/or any other appropriate combination of the foregoing ranges. As discussed below, various features of the device 100 may be adjusted in order to achieve the desired jet characteristics.

The direction of the jet 119 may be controlled by positioning the device 100 or by aiming the device outlet 109. For example, in embodiments that include rotatable modules as shown, the jet 119 may be directed by rotating the modules. For example, in the device of FIG. 2, the direction of the jet 119 may be controlled by tilting the first module 103 within the base 101 in either of the directions indicated by arrow R in FIG. 2.

In some embodiments as shown, a grinding chamber air inlet 111 may be open to the atmosphere in order to allow air to freely flow into a grinding chamber within the device 100.

The grinding chamber air inlet 111 may allow replacement air to be drawn into the grinding chamber as aerosolized salt is drawn out through a salt vent, as will be described below. For example and as shown, the grinding chamber air inlet 111 may be formed as a channel through the second module 105 to allow air to freely flow between the second module 105 and the third module 107. However, a grinding chamber air inlet need not be positioned or configured as shown. A grinding chamber air inlet may be formed at any appropriate position and in any appropriate geometric configuration to allow air to enter a grinding chamber of the device. In some embodiments where the grinding chamber air inlet 111 is disposed as shown, removal of the third module 107 from the second module 105 may allow a user to access the grinding chamber air inlet 111 more easily. Removal of the third module 107 from the second module 105 may be accomplished by removably attaching the third module 107 to the second module 105, for example using snap fits, magnets, or any other appropriate method of removable attachment.

In some embodiments as shown, a device air inlet 125 may be open to the atmosphere in order to allow air to freely flow into the device 100. For example, and as shown, the device air inlet 125 may be formed as a series of holes in a wall of the first module 103. The air supplied through the device air inlet 125 ultimately mixes with aerosolized salt in an exhaust passage of the device, as described herein. A device air inlet need not be positioned or configured as shown. A device air inlet may be formed at any appropriate position and in any appropriate geometric configuration to allow air to enter a grinding chamber of the device. For example, a single hole or vent in a wall of the device 100 is also contemplated.

In some embodiments as shown, the device 100 may include electrical components. For example, one or more buttons 113 may allow a user to operate the device, for example by selecting a mode of operation, a duration of operation, a power setting, or any other feature that may be selectable by a user. Some electrical components may provide feedback or information to a user about the operation of the device 100. For example, a light bar 115 may provide information to a user about a mode of operation, a duration of operation, a power setting or battery condition, or any other information that may be communicated to a user. Some electrical components may form part of a power system of the device. For example, a power jack 117 may be configured to receive a corresponding power cord (not shown) to provide electrical power to the device.

Figure 5:
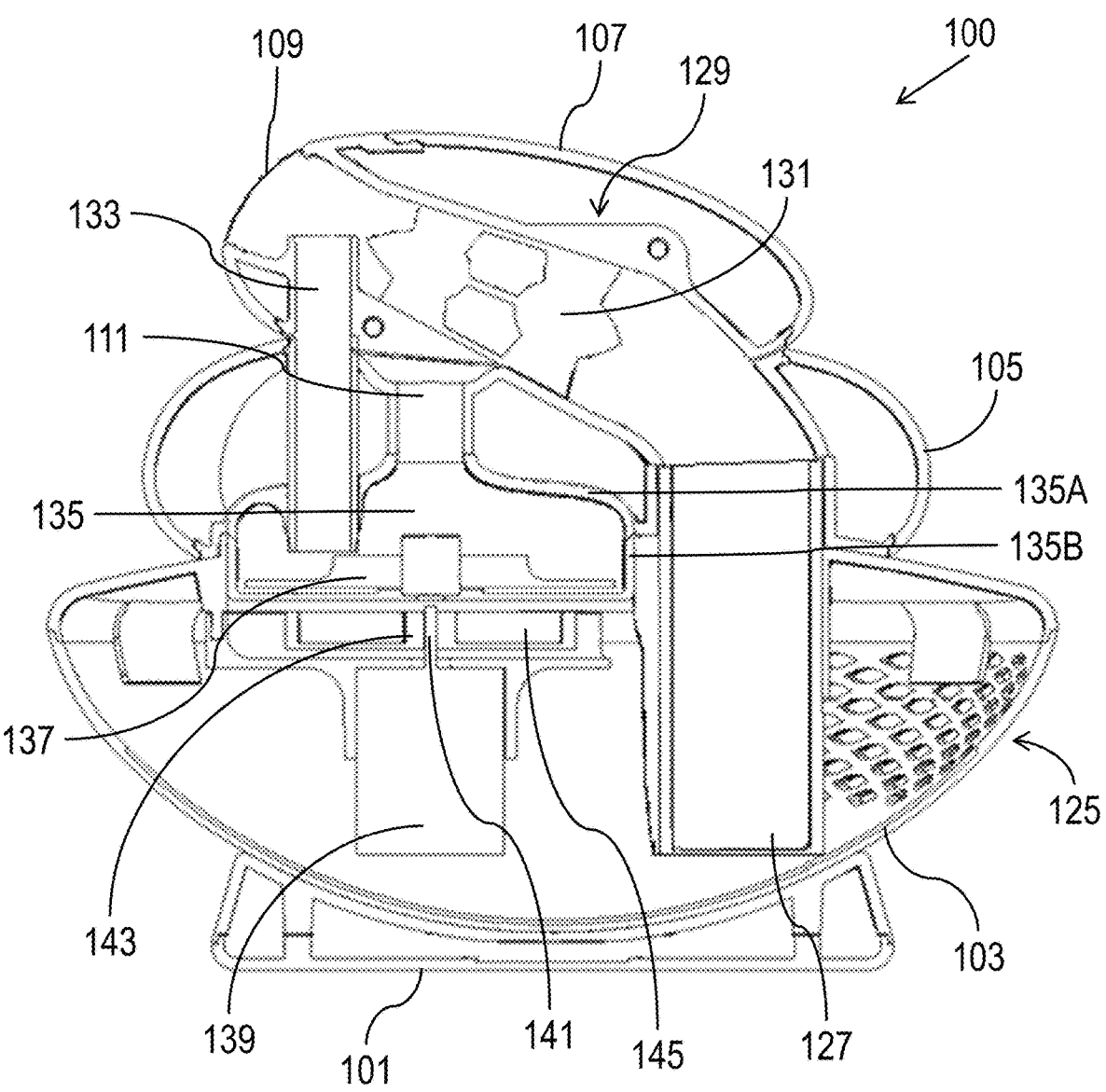
FIG. 5 is a sectional side view of the dry salt therapy device of FIG. 1 taken along line 5-5.
Figure 6:
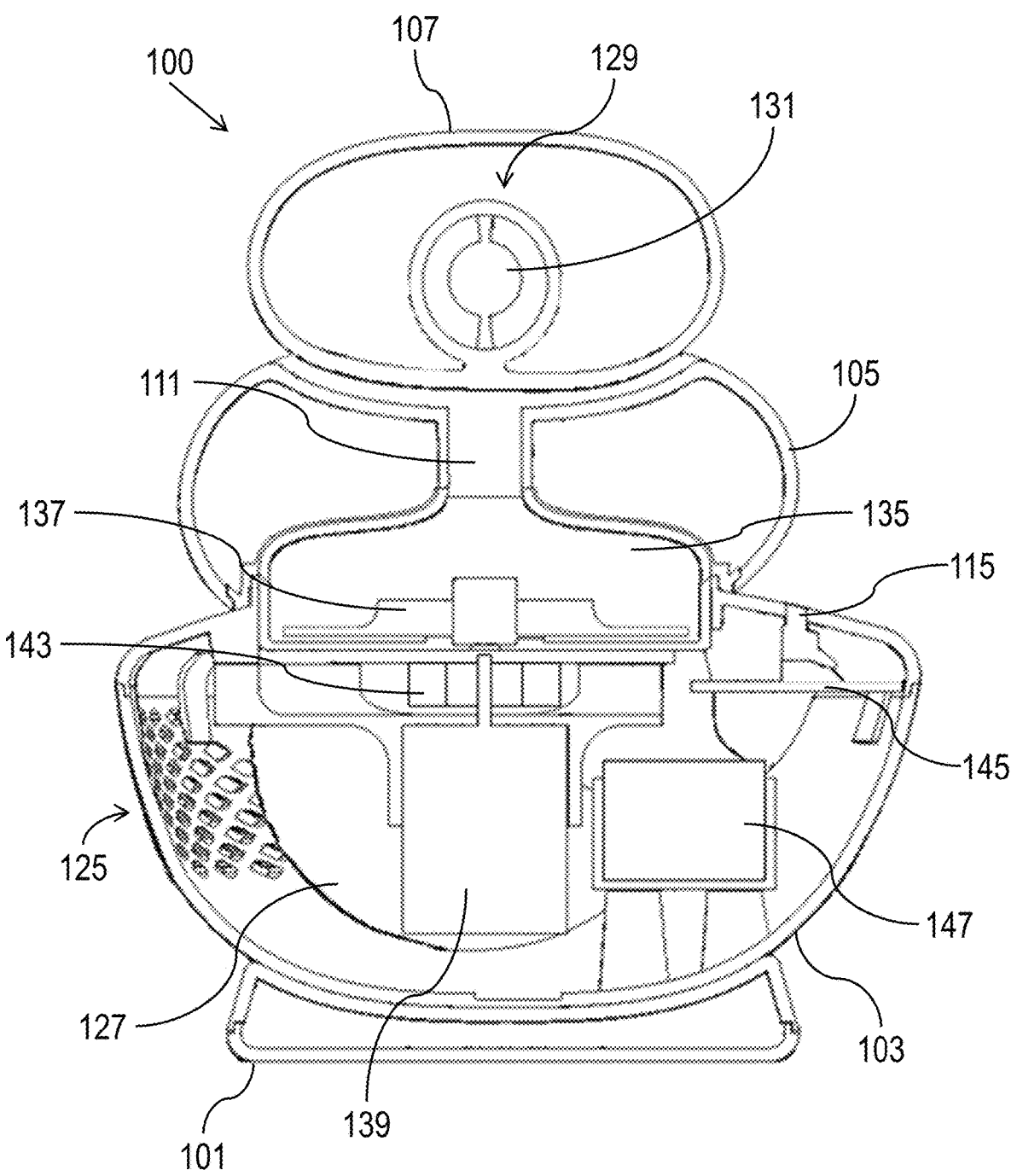
FIG. 6 is a sectional front view of the dry salt therapy device of FIG. 1 taken along line 6-6.

FIGS. 5 and 6 show the internal structure of one embodiment of the dry salt therapy device 100. In this embodiment, the first module 103 and the second module 105 cooperate to house a blower 127. The blower 127 is in fluid communication with an exhaust passage 129, which is housed within the second module 105 and the third module 107. The exhaust passage 129 terminates at the device outlet 109 and contains a flow structure 131. The exhaust passage 129 is also in fluid communication with a salt vent 133. The salt vent 133 is a fluid passageway with a first end open to a grinding chamber 135 and a second end open to the exhaust passage 129 to provide fluid communication between the grinding chamber 135 and the exhaust passage 129. The grinding chamber 135 has a grinding chamber air inlet 111 which is open to a surrounding environment to allow air to freely enter the grinding chamber 135. The grinding chamber 135 also has a grinding rotor 137 configured to spin within the grinding chamber 135. The grinding rotor 137 is coupled to a motor 139. In some embodiments as shown, the motor 139 has a rotating shaft 141 that is attached to a spinner 143. The spinner 143 includes spinner magnets 145 which are magnetically coupled with corresponding rotor magnets 153 (shown in FIG. 8), which may be contained within the grinding rotor 137. During operation, the motor 139 may cause the shaft 141 and the spinner 143 to rotate. The magnetic coupling of the spinner 143 to the grinding rotor 137 may cause the griding rotor 137 to rotate in cooperation with the spinner 143.

A user may access the grinding chamber 135 through the salt vent 133 or the grinding chamber air inlet 111. For example, a user may load a dose of salt into the grinding chamber 135 through the salt vent 133 or the grinding chamber air inlet 111. In embodiments with modules that are removably attached, for example by magnets or snap fits, a user may also access the grinding chamber 135 by removing the second module 105 from the first module 103. In such embodiments, a top portion 135A of the grinding chamber 135 may be formed as part of the second module 105, and a bottom portion 135B of the grinding chamber 135 may be formed as part of the first module 105. The top portion 135A and the bottom portion 135B may be removably attached, for example using a press fit, snap fit, or magnetic attachment. By removing the second module 105 from the first module 103, the top portion 135A may be removed from the bottom portion 135B. This may provide a user with access to the interior of the grinding chamber 135, including full access to the grinding rotor 137 to maintain, clean, or replace the grinding rotor 137. Maintenance, cleaning, or replacement of the grinding rotor 137 may be simplified by coupling the grinding rotor 137 to the motor 139 as described herein, such that the grinding rotor 137 may be removed by decoupling the rotor magnets 153 from the spinner magnets 145 and lifting the grinding rotor 137 out of the grinding chamber 135.

In some embodiments as shown in FIG. 6, the dry salt therapy device 100 may include a printed circuit board (PCB) 145 and/or other suitable control arrangement or computing device, such as a microprocessor. In one embodiment, the PCB 145 may be in electrical communication with various electrical components of the dry salt therapy device 100, including a light bar 115 and a battery 147. The PCB 145 and/or microprocessor may be programmed or configured to send information to and receive information from various components of the dry salt therapy device including the light bar 115, the battery 147 or other source of electrical power, the blower 127, the motor 139, and/or any other electrical components not shown including a timer of the device or buttons which may allow a user to control or interface with the device 100.

In some embodiments, the PCB 145, microprocessor, or other computing device may be programmed to allow a user to select a therapy duration for a dry salt therapy session. The therapy duration may be influenced by various parameters, including a level of power delivered to the blower and/or the motor, a rotation speed of the motor, an output velocity of the blower, a quantity of salt loaded into the device, or any other appropriate parameter. The PCB or microprocessor may be configured to control one or more parameters influencing the therapy duration, thereby allowing a user to select a desired therapy duration. For example, in some embodiments a dry salt therapy device may have selectable therapy durations of 5 minutes, 10 minutes, 15 minutes, 20 minutes, or any combination thereof. Of course, while particular values for the therapy duration are provided, it should be understood that other therapy durations both greater than and less than those noted are also contemplated as the disclosure is not limited in this fashion.

Figure 7:
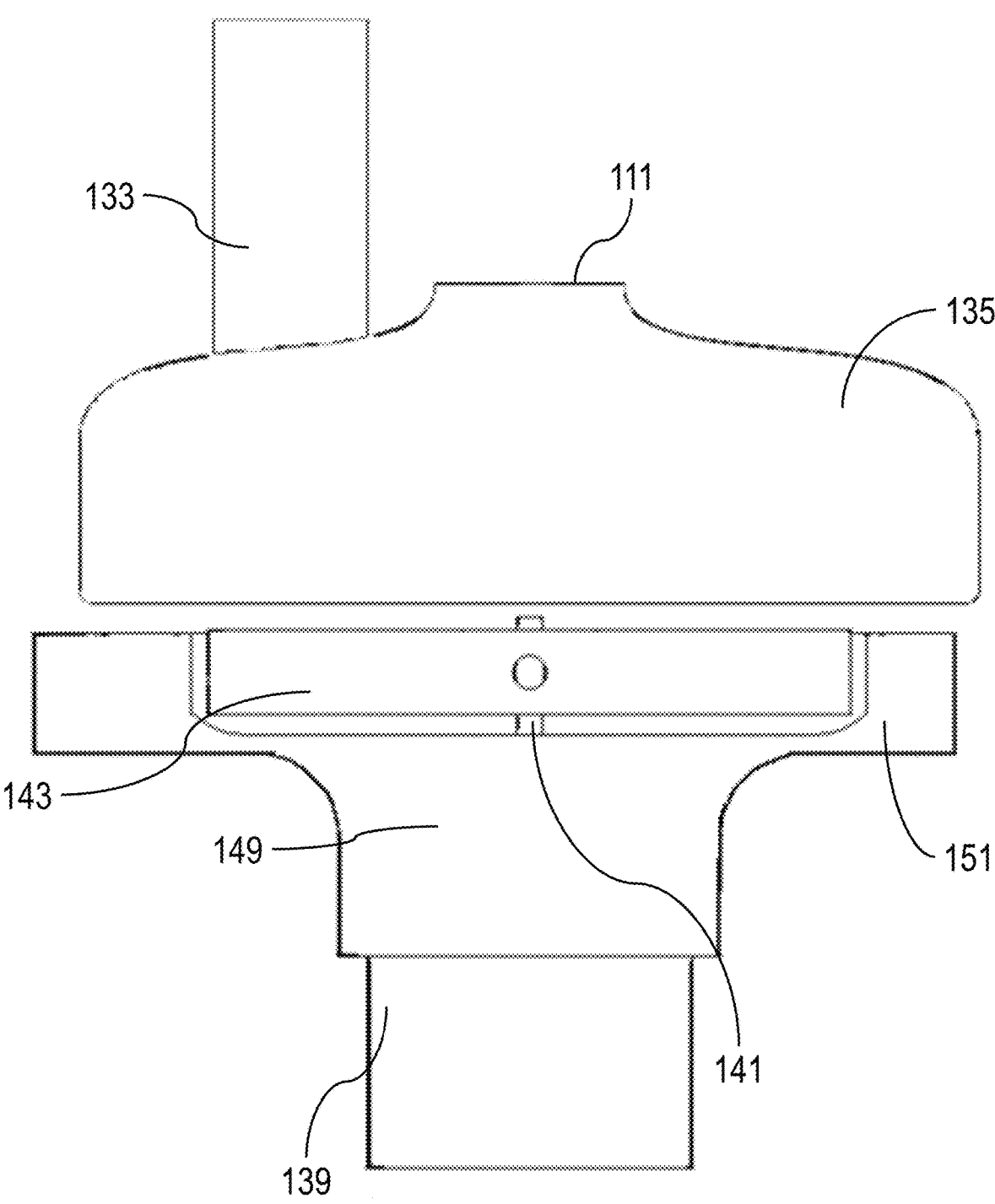
FIG. 7 is a side view of a grinding chamber, a motor mount, and a motor of the dry salt therapy device of FIG. 1.
Figure 8:
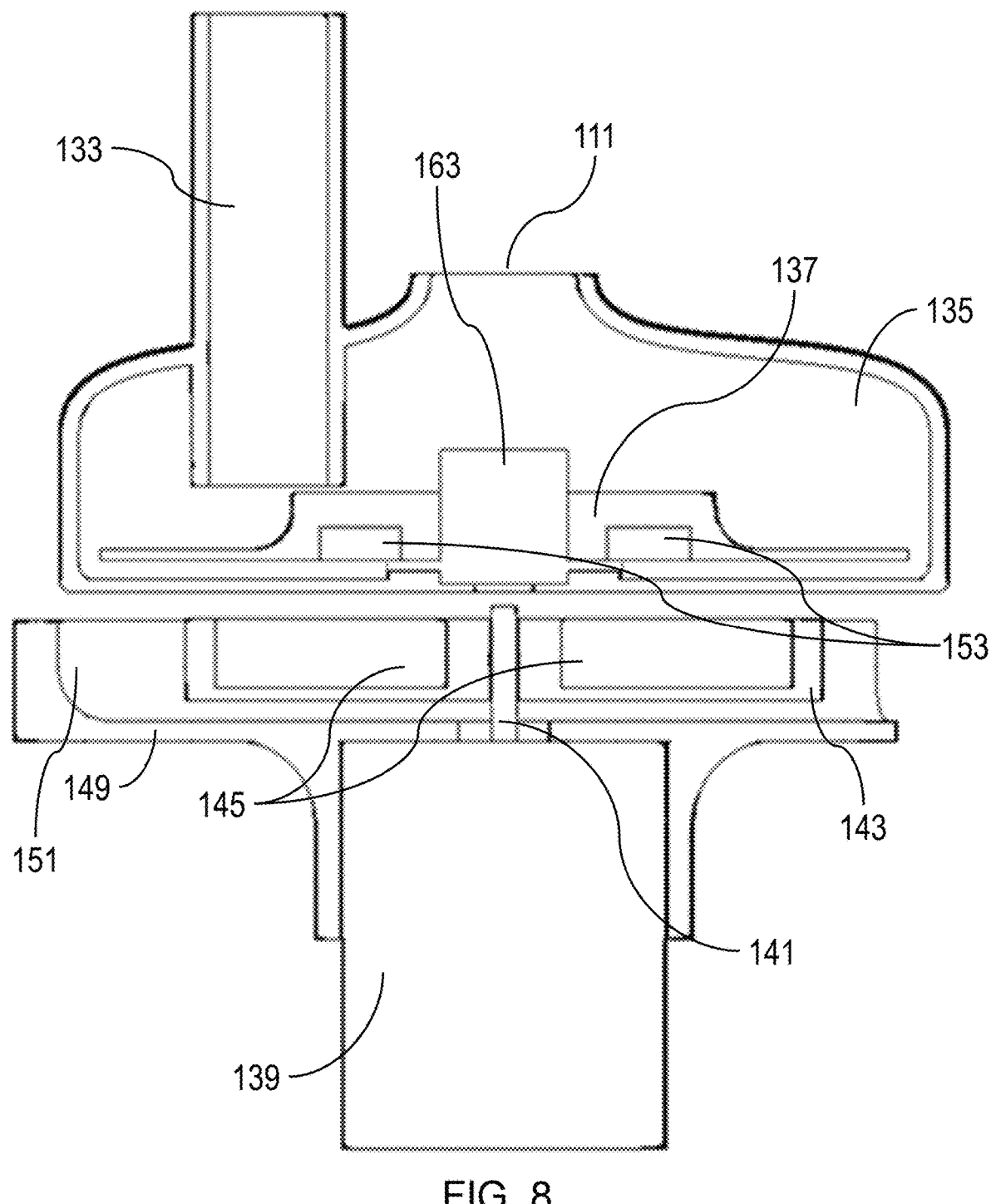
FIG. 8 is a sectional side view of the grinding chamber, the motor mount, and the motor of the dry salt therapy device of FIG. 1, taken along line 5-5.

In some embodiments as shown in FIGS. 7 and 8, the grinding chamber 135 may be mounted separately from the motor 139. The motor 139 may be mounted within a motor mount 149, which may be configured to retain the motor 139 within a housing module of the dry salt therapy device 100. The shaft 141 may extend through the motor mount 149. The motor mount 149 may also have one or more walls 151 that may form a space to accommodate the spinner 143. In some embodiments as shown in FIG. 8, the spinner 143 may contain one or more spinner magnets 145. The spinner magnets 145 may be magnetically coupled to one or more rotor magnets 153, such that rotation of the spinner 143 causes a corresponding rotation of the grinding rotor 137.

In other embodiments, the motor 139 may drive the grinding rotor 137 directly, for example by extending the shaft 141 into the grinding chamber 135 and attaching the shaft 141 to the grinding rotor 137, a rotating support member 163, or other intermediary structure to rotatably couple the shaft 141 and the grinding rotor 137. In such direct-drive embodiments, although a torque from the motor may not be delivered into the grinding chamber through magnetic coupling, the grinding rotor may still be magnetically coupled to the shaft, the rotating support member, or other intermediary structure within the grinding chamber. Retaining such magnetic coupling of the grinding rotor in a direct-drive embodiment may facilitate removal or replacement of the grinding rotor for cleaning or maintenance purposes.

Figure 9:
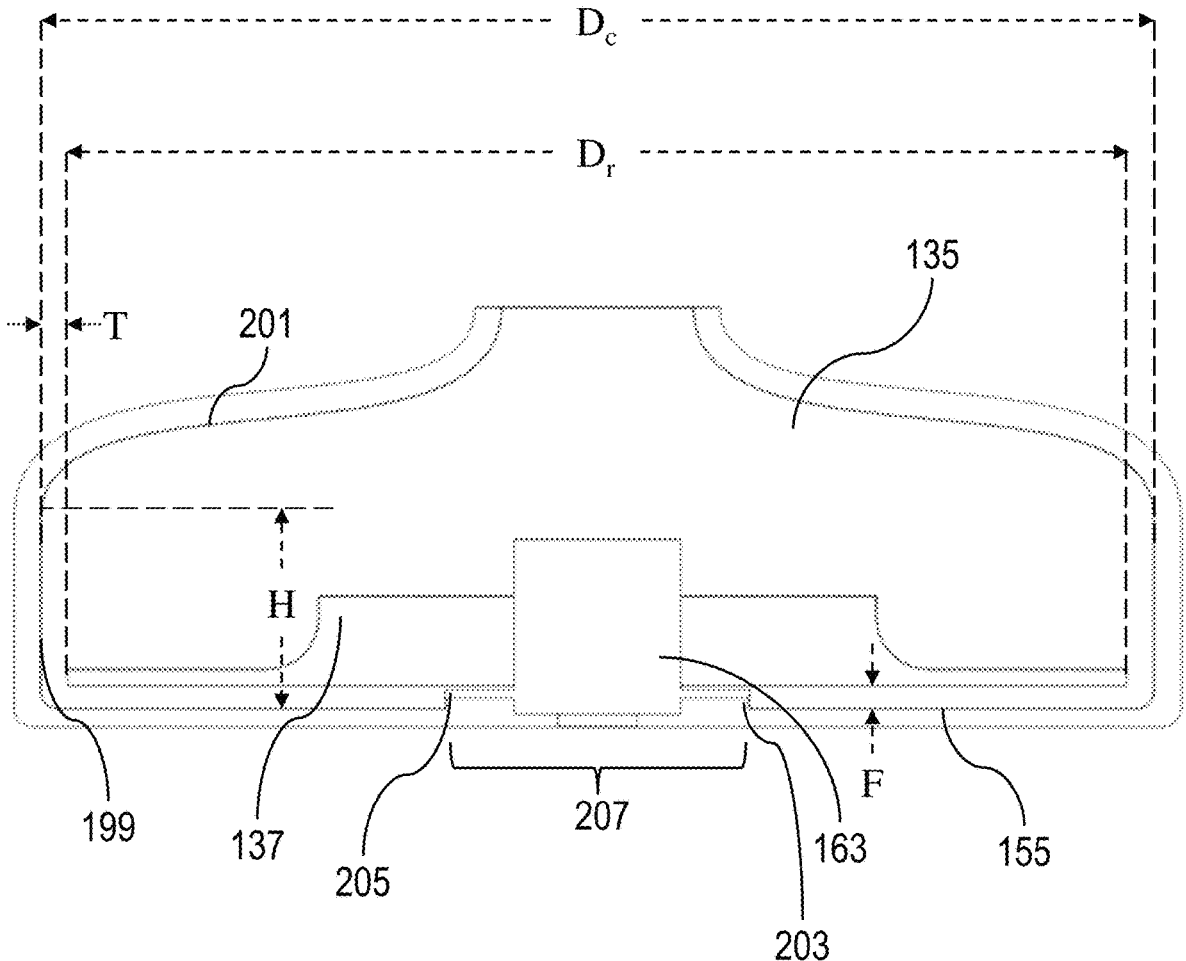
FIG. 9 is a sectional front view of a grinding chamber of the dry salt therapy device of FIG. 1, taken along line 6-6.
Figure 10:
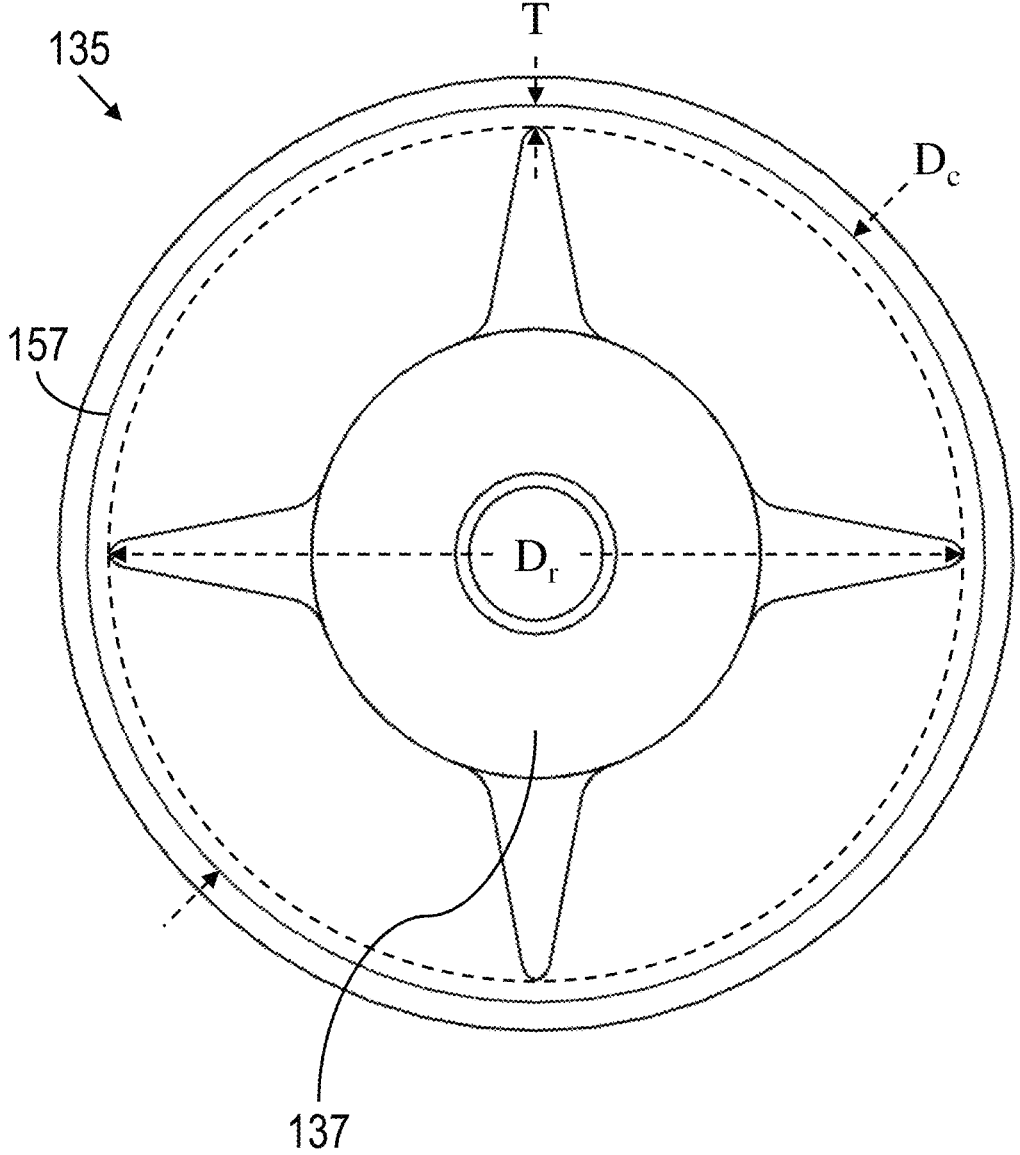
FIG. 10 is a top view of a grinding rotor within a bottom portion of a grinding chamber of the dry salt therapy device of FIG. 1.

In some embodiments as shown in FIG. 9, the grinding chamber 135 may be shaped as a hollow disc with an interior chamber diameter $D_c$ and an interior chamber height H. An aspect ratio of the grinding chamber may be defined as the ratio of the chamber diameter $D_c$ to the chamber height H (i.e., $D_c$:H). The chamber height H may be taken as any suitable measure of height within the grinding chamber. For example and as shown, in embodiments that include an interior wall 199 which curves smoothly in toward a center of the grinding chamber to form a ceiling 201, the chamber height H may be measured from a floor 155 of the grinding chamber to a point on the interior wall at which the interior wall curves toward the center to form the ceiling 201. In other embodiments that may, for example, include a ceiling and a floor which are parallel to one another, the chamber height H may be taken as the distance between the floor and the ceiling.

In some embodiments, the grinding rotor 137 may be spaced apart from the floor 155 of the grinding chamber 135 by a floor clearance F. In some embodiments, the grinding rotor 137 may be configured to rotate within a rotor diameter Dr. The rotor diameter $D_r$ may be smaller than the chamber diameter $D_c$ such that a tip of the grinding rotor 137 is spaced apart from an interior wall 157 of the grinding chamber 135 by a tip clearance T.

In some embodiments, the grinding chamber 135 may include an interface area 207 within which the rotating support member 163 may interact with the floor 155, the grinding rotor 137, or both. The rotating support member 163 may interact with the floor and/or the grinding rotor directly (e.g., by contacting them) or indirectly (e.g., using various bearings, gaskets, or clearances). The grinding chamber 135 may be configured to prevent salt from entering or accumulating in at least part the interface area 207 and interfering with interactions among the various components therein. In some embodiments, the grinding chamber floor 155 may include a ring or step that may rise toward the grinding rotor 137. In other embodiments, the rotating support member 163 may include a projection or flange which may extend radially from a center of the rotating support member. In the embodiment shown, a step 203 of the floor may cooperate with a flange 205 to prevent salt from entering or accumulating in the interface area 207 between the grinding rotor 137, thereby preventing the salt from interfering with a rotation of the grinding rotor 137.

The rate at which salt may be micronized or aerosolized within the grinding chamber 135, as well as the particle size that may be achieved therein, may be influenced by various features of the grinding chamber, including at least the aspect ratio, the floor clearance F, the tip clearance T, and a rotation speed of the grinding rotor 137. For example, a first embodiment of a grinding chamber 135 may have a high aspect ratio, a small floor clearance, and a small tip clearance, while a second embodiment may have a low aspect ratio, a large floor clearance F, and a large tip clearance T. The first embodiment may leave less space between the grinding rotor and one or more interior wall of the grinding chamber. Salt particles may therefore impact either the grinding rotor 137 or the walls more frequently in the first embodiment than in the second embodiment, resulting in faster micronization or aerosolization, as well as a smaller particle size. Additionally, the larger floor clearance F of the second embodiment may allow salt particles to fall below the grinding and accumulate there instead of being micronized or aerosolized. A third embodiment may have the same aspect ratio, floor clearance, and tip clearance as a fourth embodiment, but may have a motor 139 that is configured to rotate the grinding rotor 137 at a higher rate than the fourth embodiment. The higher rotation rate may result in a shorter micronization time in the third embodiment than in the fourth embodiment.

In some embodiments, a grinding chamber may produce a particle size greater than or equal to 0.5 microns, 1 micron, 2 microns, 3 microns, and/or any other appropriate particle size. Additionally, the particle size may be less than or equal to 1.5 microns, 2 microns, 2.5 microns, 4 microns, 5 microns, 10 microns, and/or any other appropriate particle size. Combinations of the foregoing are contemplated including, for example, greater than or equal to 0.5 microns and less than or equal to 10 microns, greater than or equal to 0.5 microns and less than or equal to 1.5 microns, and/or any other appropriate combination of the foregoing. Of course, while particular ranges for the particle size are provided above, it should be understood that other ranges both greater than and less than those noted above are also contemplated as the disclosure is not limited in this fashion.

In some embodiments, a grinding chamber may begin to achieve the desired particle size in a micronization time. The micronization time may be greater than or equal to 10 seconds, 20 seconds, 30 seconds, and/or any other appropriate time. Additionally, the micronization time may be less than or equal to 40 seconds, 50 seconds, 60 seconds, 120 seconds, and/or any other appropriate time. Combinations of the foregoing are contemplated including, for example, greater than or equal to 10 seconds and less than or equal to 120 seconds, greater than or equal to 20 seconds and less than or equal to 30 seconds, and/or any other appropriate combination of the foregoing. Of course, while particular ranges for the micronization time are provided above, it should be understood that other ranges both greater than and less than those noted above are also contemplated as the disclosure is not limited in this fashion.

In some embodiments, an aspect ratio of a grinding chamber ($D_c$:H) may be greater than or equal to approximately 1.5:1, 3:1, 4:1, 5:1, 6:1 and/or any other appropriate ratio. Additionally, the aspect ratio may be less than or equal to 7:1, 8:1, 9:1, 10:1, 15:1, and/or any other appropriate distance. Combinations of the foregoing are contemplated including, for example, greater than or equal to 1.5:1 and less than or equal to 15:1, greater than or equal to 4:1 and less than or equal to 8:1, and/or any other appropriate combination of the foregoing. Of course, while particular ranges for the aspect ratio are provided above, it should be understood that other ranges both greater than and less than those noted above are also contemplated as the disclosure is not limited in this fashion.

In some embodiments, a tip clearance ($(D_c-D_r)/2$) of a grinding chamber may be greater than or equal to 0.5 mm, 1 mm, 2 mm, 3 mm, and/or any other appropriate ratio. Additionally, the tip clearance may be less than or equal to 4 mm, 5 mm, 6 mm, 8 mm, and/or any other appropriate distance. Combinations of the foregoing are contemplated including, for example, greater than or equal to 0.5 mm and less than or equal to 8 mm, greater than or equal to 1 mm and less than or equal to 5 mm, and/or any other appropriate combination of the foregoing. Of course, while particular ranges for the tip clearance are provided above, it should be understood that other ranges both greater than and less than those noted above are also contemplated as the disclosure is not limited in this fashion.

In some embodiments, a floor clearance of a grinding chamber may be greater than or equal to 0.5 mm, 1 mm, 2 mm, 3 mm, and/or any other appropriate ratio. Additionally, the floor clearance may be less than or equal to 4 mm, 6 mm, 8 mm, and/or any other appropriate distance. Combinations of the foregoing are contemplated including, for example, greater than or equal to 0.5 mm and less than or equal to 8 mm, greater than or equal to 1 mm and less than or equal to 4 mm, and/or any other appropriate combination of the foregoing. Of course, while particular ranges for the floor clearance are provided above, it should be understood that other ranges both greater than and less than those noted above are also contemplated as the disclosure is not limited in this fashion.

In some embodiments, a rotation speed of a grinding rotor may be greater than or equal to 1,000 RPM, 2,000 RPM, 3,000 RPM, 25,000 and/or any other appropriate ratio. Additionally, the rotation speed may be less than or equal to 3,500 RPM, 4,000 RPM, 4,200 RPM, 4,500 RPM, 50,000 RPM and/or any other appropriate speed. Combinations of the foregoing are contemplated including, for example, greater than or equal to 1,000 RPM and less than or equal to 50,000 RPM, greater than or equal to 25,000 RPM and less than or equal to 50,000 RPM, greater than or equal to 3,000 RPM and less than or equal to 4,500 RPM, and/or any other appropriate combination of the foregoing. Of course, while particular ranges for the rotation speed are provided above, it should be understood that other ranges both greater than and less than those noted above are also contemplated as the disclosure is not limited in this fashion. It will be appreciated that any appropriate type of motor (e.g., servo motors, brushed motors, brushless motors, direct drive motors, or any other appropriate motors) may be selected to produce a desired range of RPM for a given embodiment. For example, a servo motor may be used to produce 3,000-5,000 RPM in one embodiment, while a brushless motor may be used to produce 25,000-50,000 RPM in another embodiment.

Figure 11A:
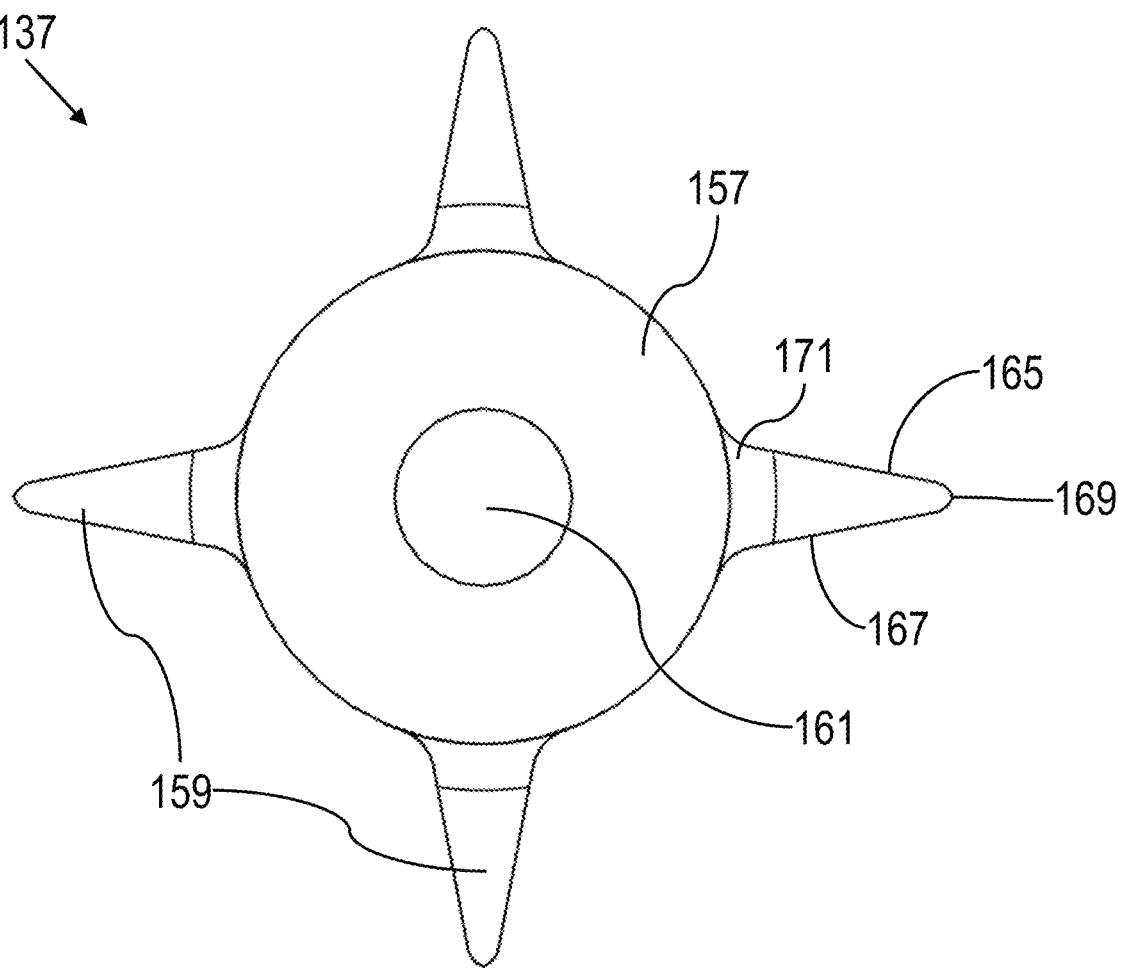
FIG. 11A is a top view of the grinding rotor of the dry salt therapy device of FIG. 1.
Figure 11B:
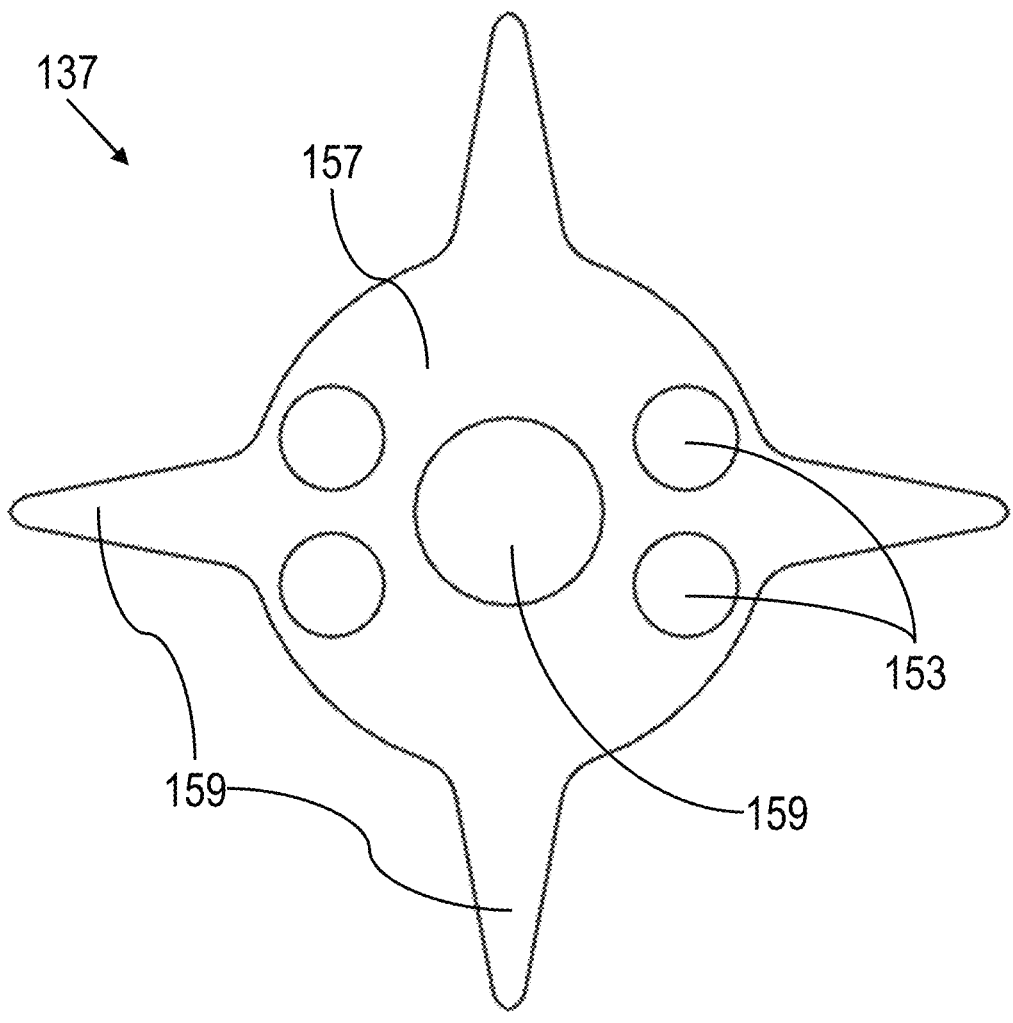
FIG. 11B is a bottom view of the grinding rotor of the dry salt therapy device of FIG. 1.

In some embodiments as shown in FIGS. 11A and 11B, a grinding rotor 137 may comprise a hub portion 157 and one or more blades 159 extending radially from the hub portion 157. In the embodiment shown, the hub portion 157 may have a hole 161 formed therein to allow the grinding rotor 137 to cooperate with a rotating support member 163 (shown in FIG. 9). In some embodiments, the rotating support member 163 and the shaft 141 may be the same element. In other embodiments as shown, the rotating support member 163 and the shaft 141 may be different elements. Still further embodiments may not include a rotating support member 163, and the grinding rotor 137 may be retained axially and rotated through the magnetic coupling of the rotor magnets 153 and the spinner magnets 145.

Each of the one or more blades 159 may have a first edge 165, a second edge 167, a tip portion 169, and a root portion 171. The root portion 171 may be the portion of the blade 159 that attaches to the hub portion 157. The root portion 171 may attach to the hub portion 157 in any appropriate configuration. For example, the root portion 171 and blade 159 may be formed as a single piece with the hub portion 157. The root portion 171 may have one or more radii at the interface with the hub portion 157, or it may attach at an angle. The tip portion 169 may be the portion of the blade 159 that is furthest from the hub portion 157. The tip portion 169 may be blunt, sharp, rounded, flat, pointed or any other appropriate geometry. The first edge 165 and the second edge 167 may be on opposing sides of a length of the blade 159 that extends between the root portion 171 and the tip portion 169. The first edge 165 and the second edge 167 may be blunt, sharp, rounded, flat, serrated, curved, angled, or any other appropriate geometry. The first edge 165 and the second edge 167 may have the same geometry or different geometries. One of the first edge 165 and the second edge 167 may be a leading edge, and the other may be a trailing edge, depending upon a direction of rotation of the grinding rotor 137. In some embodiments as shown in FIG. 11B, the grinding rotor 137 may include one or more rotor magnets 153. The rotor magnets may be contained in the grinding rotor 137 by the use of adhesives, press fit, snap fit, or any other appropriate method. The rotor magnets 153 may be located in the hub portion 157, or any other appropriate location in the grinding rotor 137, including a root portion 171 of a blade 159. The rotor magnets 153 may be configured to magnetically couple to one or more corresponding spinner magnets 145 (shown in FIG. 8). The grinding rotor 153 may be formed of plastic, metal, or any other appropriate material.

Figures 12A, 12B:
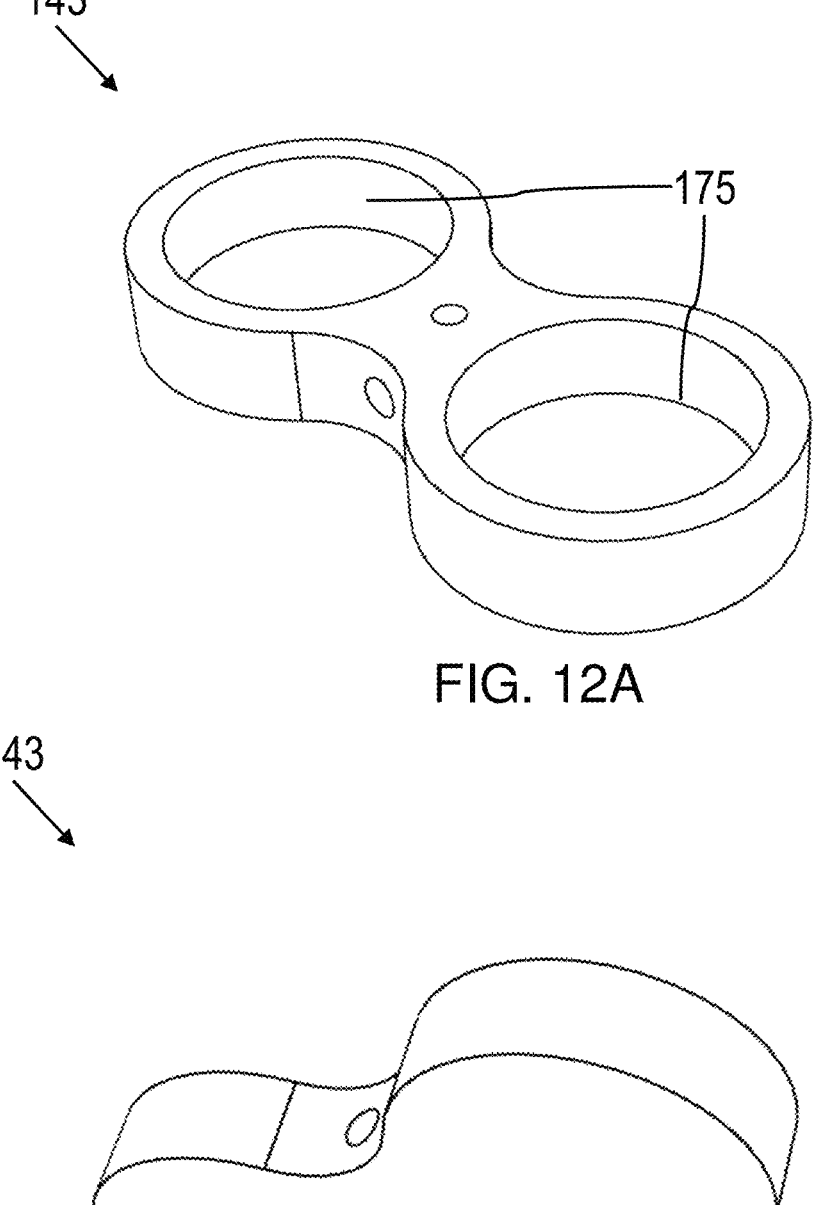
FIG. 12A is a top perspective view of a spinner of the dry salt therapy device of FIG. 1.
FIG. 12B is a bottom perspective view of the spinner of the dry salt therapy device of FIG. 1.

As discussed above, a shaft 141 of the motor 139 may be attached to a spinner 143 which is magnetically coupled to the grinding rotor 137, such that operation of the motor 139 may rotate the grinding rotor 137. In some embodiments as shown in FIGS. 12A and 12B, the spinner 143 may comprise a spinner body 173 and one or more spinner magnet recesses 175 configured to receive spinner magnets 145. The spinner magnets 145 may be configured to magnetically couple to one or more corresponding rotor magnets 153 (shown in FIGS. 8 and 11B). The spinner magnets 145 may be contained in the spinner recesses 175 by the use of adhesives, press fit, snap fit, or any other appropriate method. The spinner 143 may also comprise a shaft hole 177 formed in the spinner body 173 to receive a shaft 141 of a motor 139 (shown, for example, in FIG. 8). The shaft hole 177 may extend completely through the spinner body 173 (i.e., the shaft hole 177 may be a through-hole), or the shaft hole 177 may extend only partially through the spinner body 173.

Figure 13A:
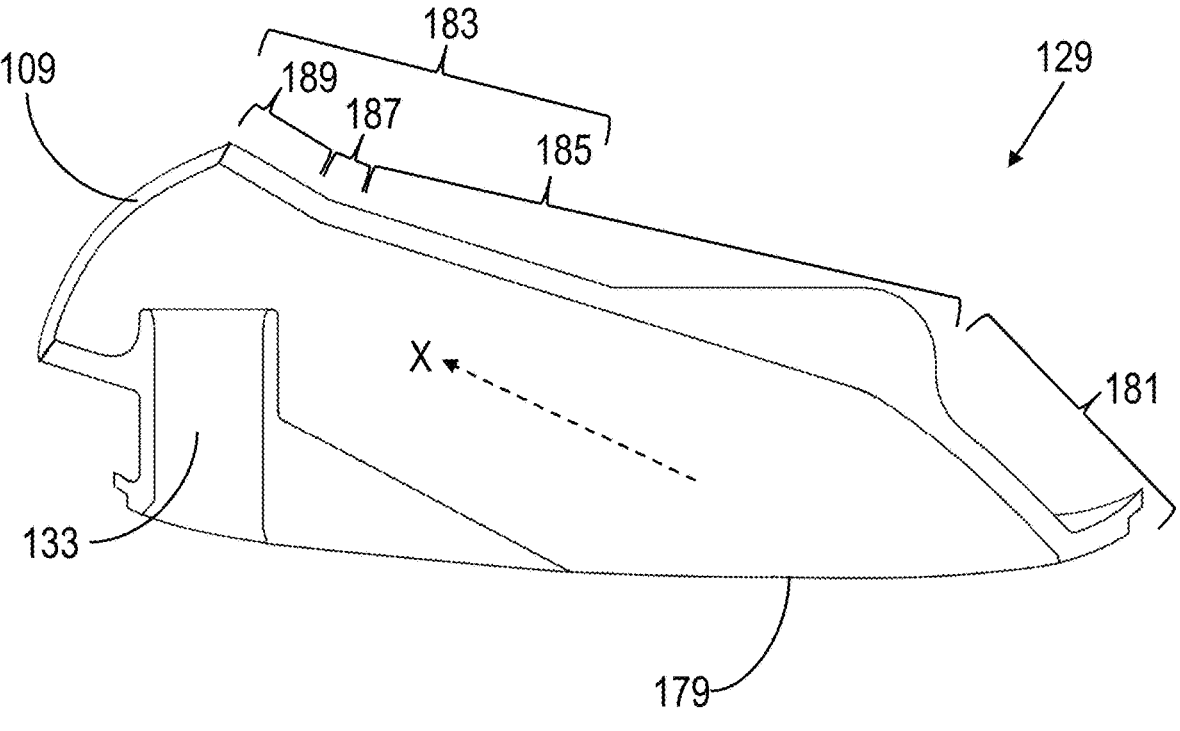
FIG. 13A is a sectional side view of an exhaust passage of the dry salt therapy device of FIG. 1, taken along line 5-5 and with a flow structure of the device removed.
Figure 13B:
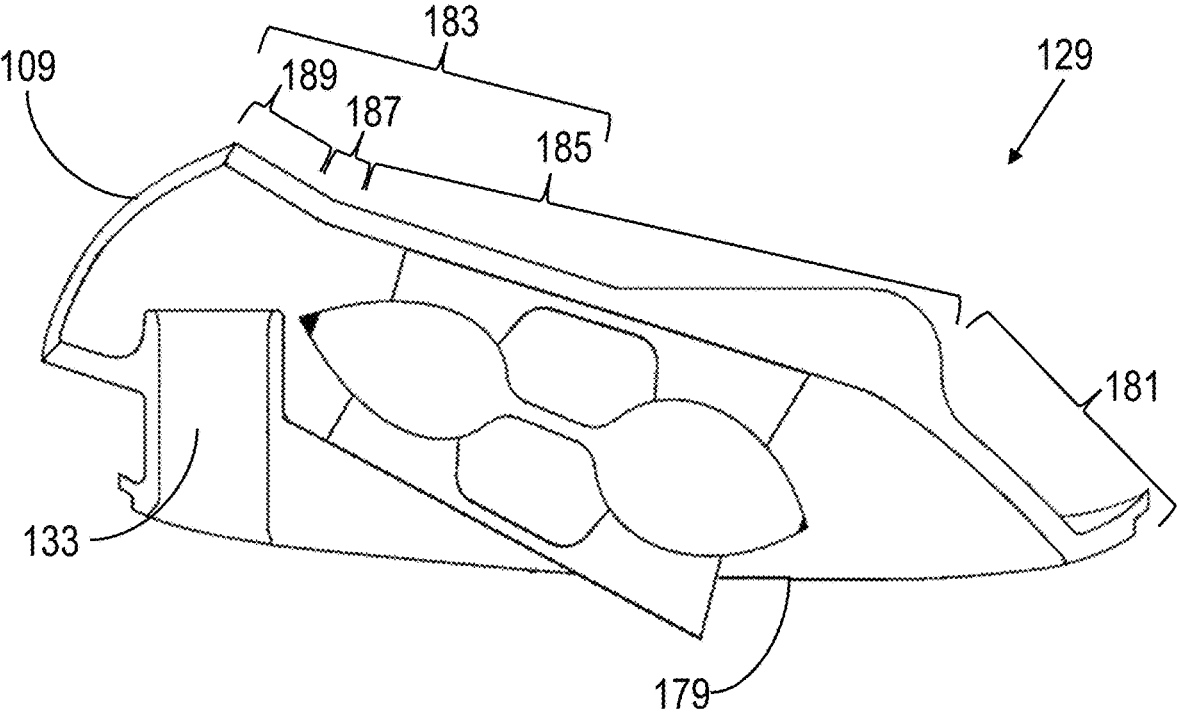
FIG. 13B is a sectional side view of an exhaust passage of the dry salt therapy device of FIG. 1, taken along line 5-5 and with the flow structure of the device included.

As described herein, the exhaust passage 129 may permit aerosolized salt to be mixed with air and ejected from the device 100 by providing fluid communication between the blower 127, the grinding chamber 135, and the device outlet 109. In some embodiments as shown in FIGS. 13A and 13B, the exhaust passage 129 may be a pipe-like or tube-like element configured to allow a flow of air to pass therethrough. For example as shown in FIG. 13A, during operation of a dry salt therapy device, the flow of air may pass in the direction of arrow X. A cross-section of the exhaust passage 129 may be circular, elliptical, or may have any appropriate number of sides (i.e., the cross-section may be quadrangular, hexagonal, octagonal, etc.). A width, diameter, or cross-sectional area of the exhaust passage 129 may be constant or may vary along a length of the exhaust passage 129, as described below. In some embodiments as shown, the exhaust passage 129 may comprise an exhaust passage inlet 179, a device outlet 109, an entrance section 181, a converging-diverging (CD) nozzle 183, and a salt vent 133.

The exhaust passage inlet 179 may be fluidly coupled to an outlet of a blower 127 (shown in FIGS. 5 and 15), such that a flow of air generated by the blower 127 passes into the exhaust passage inlet 179. The entrance section 181 may connect the exhaust passage inlet 179 to the CD nozzle 183. The entrance section 181 may be straight, or may include one or more bends, or may be formed in any appropriate geometry. The CD nozzle 183 may comprise a converging section 185, a throat section 187, and a diverging section 189.

The converging section 185 may be fluidly coupled with the entrance section 181 at an upstream end and with the throat section 187 at a downstream end. A cross-sectional area of the converging section 185 may decrease along a direction of airflow, such that the cross-sectional area of the converging section 185 is at a maximum near the upstream end and a minimum near the downstream end.

The throat section 187 may be fluidly coupled with the converging section 185 at an upstream end and with the diverging section 189 at a downstream end. A cross-sectional area of the CD nozzle 183 may reach a minimum within the throat section 185.

The diverging section 189 may be fluidly coupled with the throat section 187 at an upstream end and with the device outlet 109 at a downstream end. A cross-sectional area of the diverging section 189 may increase along a direction of airflow, such that the cross-sectional area of the diverging section 189 is at a minimum near the upstream end and a maximum near the downstream end. The diverging section 189 may terminate with the device outlet 109.

The salt vent 133 may comprise a duct providing fluid communication between the grinding chamber 135 and the exhaust passage 129, such that air and/or aerosolized salt may flow between the grinding chamber 135 and the exhaust passage 129. The salt vent 133 may comprise a hole in a wall of the exhaust passage 129, or it may protrude from a wall of the exhaust passage 129 into the flow of air as shown. The salt vent 133 may protrude from a wall of the exhaust passage 129 to a point at or near the center of the flow of air. The salt vent 133 may be located at any point along the exhaust passage 129. For example, the salt vent 133 may be located within the entrance section 181, the converging section 185, the throat section 187, the diverging section 189, or it may be located at the device outlet 109. In some embodiments as shown, the salt vent 133 may be disposed at an upstream end of the throat section 187.

In some embodiments as shown in FIG. 13B, the exhaust passage 129 may additionally include a flow structure 131. The flow structure 131 may be configured to obtain a desired characteristic in the flow of air through the exhaust passage 129. For example, the flow structure 131 may be configured to reduce a turbulence within the flow of air or to influence a velocity of the flow of air. The flow structure 131 may be disposed at any point along the exhaust passage 129. For example, the flow structure 131 may be located within the entrance section 181, the converging section 185, the throat section 187, the diverging section 189, or it may be located at the device outlet 109. In some embodiments as shown, the flow structure 131 may be disposed in the converging section 185 immediately upstream of the salt vent 133. Some embodiments may use multiple flow structures disposed at multiple points along the exhaust passage 129.

Figures 14A, 14B:
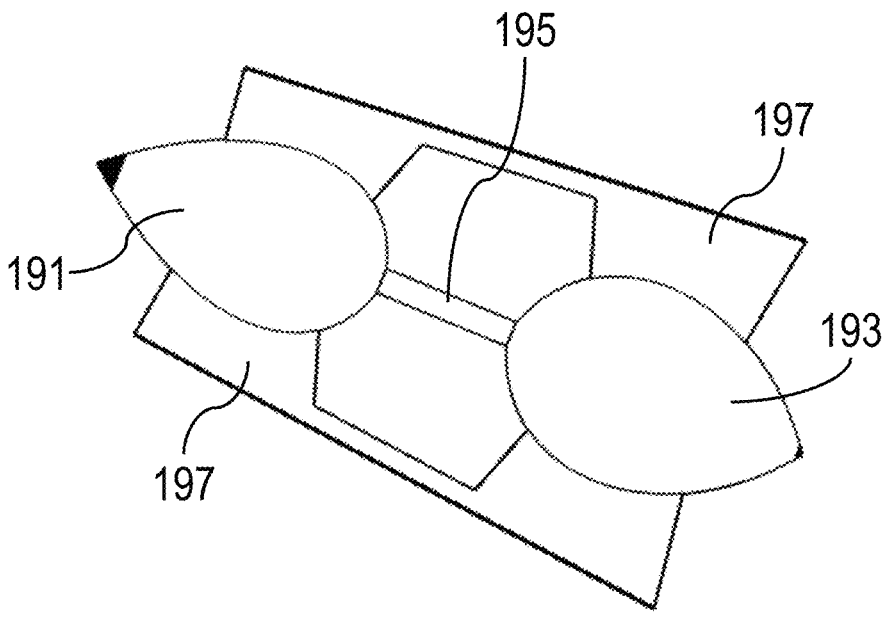
FIG. 14A is a side view of the flow structure of the dry salt therapy device of FIG. 1.
FIG. 14B is a front perspective view of the flow structure of the dry salt therapy device of FIG. 1.

The flow structure 131 may be formed in any appropriate geometric configuration. In some embodiments as shown in FIGS. 14A and 14B, a flow structure 131 may comprise a first teardrop body 191 and a second teardrop body 193, each of the first and second teardrop bodies having a tapered end and a rounded end. The rounded ends may be axially connected by an elongate member 195. The flow structure may further comprise one or more tabs 197 configured to seat the flow structure 131 within the exhaust passage 129. The flow structure 131 may be seated in the exhaust passage 129 by the use of adhesives, press fit, snap fit, or any other appropriate method. The flow structure 131 may be aligned with the flow of air such that the tapered end of the first teardrop body 191 points in an upstream direction and the tapered end of the second teardrop body 193 points in a downstream direction.

Figure 15:
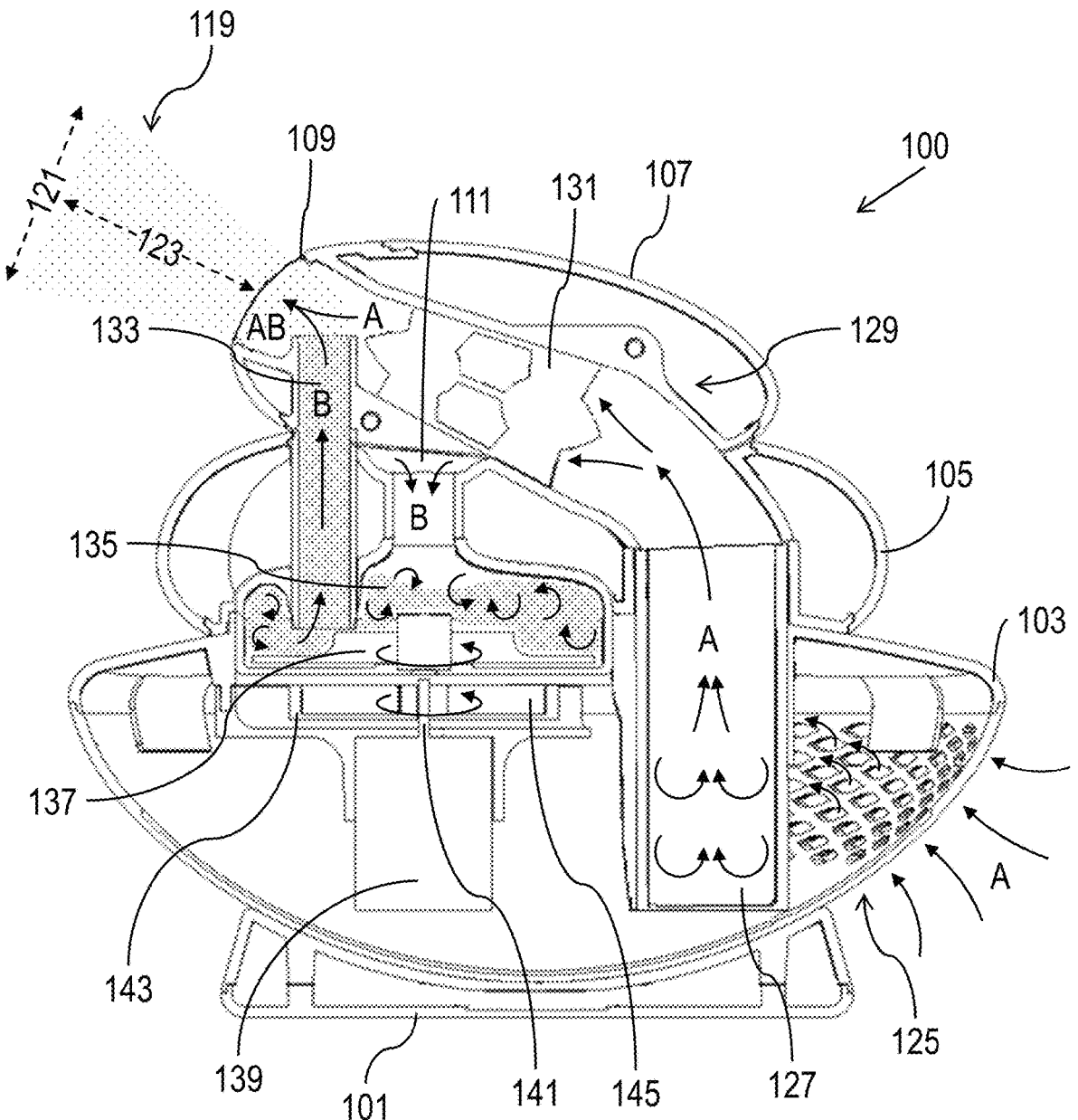
FIG. 15 is a sectional side view of the dry salt therapy device of FIG. 1, taken along line 5-5, with flow paths illustrated schematically.

Having described the structure of one embodiment of a dry salt therapy device 100, the operation and airflow of the dry salt therapy device 100 will now be described with reference primarily to FIG. 15.

A dose of salt may be loaded into a grinding chamber 135. The salt may be common table salt, sea salt, rock salt, granulated salt, or any other form of salt suitable for micronization or aerosolization. The salt may be loaded into the grinding chamber 135 through the salt vent 133 or the grinding chamber air inlet 111. The salt vent 133 may be accessible to a user through an opening formed by a device outlet 109. The grinding chamber air inlet 111 may be accessible through a channel formed in a second module 105 as described above. Alternatively or additionally, the third module 107 may be removed from the second module 105 to permit more direct access to both the salt vent 133 and the grinding chamber air inlet 111. Alternatively or additionally, the second module 105 may be removed from the first module 103 to remove an upper portion 135A from a lower portion 135B, as shown and described in FIG. 5. A dose of salt may be loaded into the grinding chamber by any suitable method, as the disclosure is not limited in this way.

A motor 139 and a blower 127 may be powered on individually or they may be powered on together, as by a user's operation of a single button. The motor 139 and the blower 127 may be powered on at the same time or at different times. For example, the motor 139 may be powered on prior to the blower 127, and the blower 127 may be powered on after a delay. The delay may be predetermined and/or programmed into a PCB of the device 100, such that a single power switch may power on the motor 139 and then the blower 127 after a predetermined delay. The delay may also be controlled by a user. For example, a user may operate separate power switches for each of the motor 139 and the blower 127. Such a delay may allow at least some of the salt to be micronized or aerosolized prior to the blower 127 being powered on.

When the motor 139 is in operation, it may cause a grinding rotor 137 to spin within the grinding chamber 135. The motor 139 may be connected to a spinner by a shaft 141. The spinner may include one or more spinner magnets 145, which may be magnetically coupled with one or more rotor magnets disposed in the grinding rotor 137. Rotation of the spinner 143 by the motor 139 may therefore cause corresponding rotation of the grinding rotor 137, thereby causing the salt to be micronized or aerosolized.

When the blower 127 is powered on, two flow paths may be generated through the device 100. A first flow path A may begin with a flow of air entering the device 100 through a device air inlet 125 due to a suction force caused by operation of the blower 127. The first flow path A may continue from the device air inlet 125 through the blower 127 and into the exhaust passage 129. In some embodiments as shown, the exhaust passage 129 may include a flow structure 131 and/or a CD nozzle as shown and described in FIGS. 13A and 13B. The salt vent 133 may be open to the exhaust passage 129 and may provide fluid communication between the exhaust passage 129 and the grinding chamber 135 in addition to providing an opening through which salt may loaded into the grinding chamber 135.

A second flow path B may enter the grinding chamber 135 through the grinding chamber air inlet 111, and may pass through the grinding chamber 135, through the salt vent 133, and into the exhaust passage 129. The second flow path B may carry the aerosolized salt out of the grinding chamber 135 and into the exhaust passage 129 through the salt vent 133. The first flow path A and the second flow path B may merge in the exhaust passage 129 to form a combined flow path AB. The combined flow path AB may carry the aerosolized salt out of the dry salt therapy device 100 through the device outlet 109.

The second flow path B may be generated at least in part by a pressure difference between the exhaust passage 129 and the grinding chamber 135. A velocity in the first flow path A may cause a pressure within the exhaust passage 129 to decrease. The reduction in pressure may cause the pressure in the exhaust passage 129 to be lower than a pressure in the grinding chamber 135. The higher pressure in the grinding chamber 129 may cause air to flow through the salt vent 133 and into the lower pressure environment of the exhaust passage 129. It will be appreciated that a greater pressure difference across the salt vent 133 may result in a greater flow rate of air and/or aerosolized salt through the salt vent 133.

The relative configurations of at least the flow structure 131, the exhaust passage 129, and the salt vent 133 may influence the pressure difference. For example, the exhaust passage 129 may be configured as a CD nozzle, as described above in relation to FIG. 13A, in order to produce a maximum velocity and a minimum pressure within a throat section of the CD nozzle. The flow structure 131 may be positioned within a converging section of the CD nozzle and may be configured to further accelerate the first flow path A and/or to reduce a turbulence within the exhaust passage 129, thereby creating a more uniform velocity profile and a more consistent pressure difference near the salt vent 133, thereby producing a more consistent flow rate therethrough. By positioning the salt vent 133 at or near the throat section, the pressure difference across the salt vent 133, and therefore the flow rate therethrough, may be maximized.

The pressure difference may be further influenced by the position of the salt vent 133 with respect to the cross section of the first flow path A. It will be appreciated that the velocity of the first flow path A may be greater near the center of flow, furthest from one or more walls of the exhaust passage 129. Therefore, the pressure difference and resulting flow rate through the salt vent 133 may be increased by configuring the salt vent 133 to protrude from a wall of the exhaust passage 129 into the center of the flow.

The blower 127 may also be selected to influence the pressure difference. For example, it will be appreciated that a stronger blower may increase the velocity of the first flow path A, thereby increasing the pressure difference and the flow rate within the salt vent as compared to a weaker blower. It will be appreciated that a flow structure may be included to reduce any additional turbulence that may result from the increased velocity, thereby maintaining a more consistent velocity and pressure within the exhaust passage.

The aerosolized salt in the combined flow path AB may be carried out of the device outlet 109 in a jet 119. The jet 119 may have a jet diameter 121 which may vary along a distance 123 from the device outlet 109. The device 100 may be configured to produce a jet 119 having a desired diameter 121 at a desired distance 123, as described above in relation to FIG. 2. The diameter 121 and distance 123 of the jet 119 may be influenced by the configuration and structure of at least the exhaust passage 129, the flow structure 131, the device outlet 109, and the blower 127. For example, a first embodiment of a dry salt therapy device may include an exhaust passage 129 that is configured as a CD nozzle, and a flow structure 131 that is configured to further accelerate and/or to reduce a turbulence within a flow of air in a converging section of the CD nozzle. A second embodiment may include an exhaust passage 129 that is configured as a diverging nozzle or a diffuser, with a flow structure 131 that is configured to decelerate the flow of air. The first embodiment may produce a jet 119 that travels a greater distance 123 or has a smaller diameter 121 at a given distance 123 than the second embodiment. Alternatively, a third embodiment may have a more powerful blower 127 than a fourth embodiment. The exhaust passage 129 and flow structure(s) 131 may be identical between the third and fourth embodiments. The third embodiment may produce a jet 119 that travels a greater distance 123 than the fourth embodiment. The direction of the jet 119 may be controlled by positioning the device 100 or by aiming the device outlet 109 as described above with reference to FIG. 2.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A dry salt therapy device comprising:
   a blower;
   an exhaust passage fluidly coupled to the blower, the exhaust passage comprising a converging-diverging nozzle including a converging section, a throat section, and a diverging section;
   a grinding chamber configured to aerosolize salt;
   a salt vent configured to fluidly couple the exhaust passage and the grinding chamber; and
   a grinding chamber air inlet positioned upstream from the salt vent, the grinding chamber air inlet configured to fluidly couple the exhaust passage and the grinding chamber, wherein the grinding chamber air inlet is configured to flow air from the exhaust passage into the grinding chamber and into the salt vent,
   wherein the device is divided into a plurality of housing modules that are configured to be removable from one another, wherein a first module includes a bottom portion of the grinding chamber, and a second module includes a top portion of the grinding chamber, such that removal of the second module also removes the top portion of the grinding chamber.

2. The device of claim 1, wherein the diverging section terminates at an outlet of the device.

3. The device of claim 1, wherein a cross-section of the converging-diverging nozzle is circular along at least a portion of a length of the converging-diverging nozzle.

4. The device of claim 1, wherein the converging-diverging nozzle is configured to increase a pressure difference between the grinding chamber and the exhaust passage.

5. The device of claim 1, wherein the exhaust passage is configured to permit aerosolized salt to be ejected from the device.

6. The device of claim 1, wherein the exhaust passage is configured to eject a jet of aerosolized salt from an outlet of the device and deliver the jet to a user who is not in contact with the device.

7. The device of claim 6, wherein a diameter of the jet is between about 4 inches and about 8 inches at a distance of about 2 feet to about 4 feet from the outlet, and wherein the converging-diverging nozzle is configured to facilitate generation of the jet.

8. The device of claim 1, wherein the salt vent is disposed at or near the throat section of the converging-diverging nozzle.

9. The device of claim 8, wherein the salt vent protrudes from a wall of the exhaust passage into a center of a flow of air through the exhaust passage.

10. The device of claim 1, further comprising an entrance section disposed downstream of the blower and upstream of the exhaust passage and wherein the entrance section includes at least one bend.

11. The device of claim 1, wherein the exhaust passage contains a flow structure configured to modify a flow of air through the exhaust passage.

12. The device of claim 1, wherein the plurality of housing modules are configured to rotate with respect to one another in at least one direction.

13. The device of claim 1, wherein at least one feature of the grinding chamber is configured to reduce a particle size of a dose of salt to between 0.5 microns and 1.5 microns, the at least one feature being selected from the group consisting of: a grinding chamber aspect ratio, a floor clearance of a grinding rotor of the grinding chamber, a tip clearance of the grinding rotor of the grinding chamber, and a rotation speed of the grinding rotor of the grinding chamber.

14. The device of claim 1, wherein at least one feature of the grinding chamber is configured to reduce a particle size of a dose of salt to between 0.5 microns and 2.5 microns, the at least one feature being selected from the group consisting of: a grinding chamber aspect ratio, a floor clearance of a grinding rotor of the grinding chamber, a tip clearance of the grinding rotor of the grinding chamber, and a rotation speed of the grinding rotor of the grinding chamber.

15. The device of claim 11, wherein the flow structure includes a first teardrop body that points in an upstream direction and a second teardrop body that points in a downstream direction towards the blower.

16. The device of claim 11, wherein the flow structure is configured to modify the flow of air through the exhaust passage by modifying at least one of a turbulence within the flow of air or a velocity of the flow of air.

17. The device of claim 1, wherein the second module includes a grinding rotor.

18. The device of claim 1, wherein the dry salt therapy device is configured to receive a dose of salt through at least one of the salt vent and the grinding chamber air inlet.

19. A dry salt therapy device comprising:

a blower;

an exhaust passage fluidly coupled to the blower, and containing a flow structure configured to modify a flow of air through the exhaust passage, the exhaust passage comprising a converging-diverging nozzle including a converging section, a throat section, and a diverging section;

a grinding chamber configured to aerosolize salt;

a salt vent disposed at or near the throat section of the converging-diverging nozzle and configured to fluidly couple the exhaust passage and the grinding chamber, wherein the salt vent protrudes from a wall of the exhaust passage into a center of a flow of air through the exhaust passage, and wherein the flow structure includes a first teardrop body that points in an upstream direction and a second teardrop body that points in a downstream direction towards the blower.

\* \* \* \* \*